US010209257B2

(12) United States Patent
Valenta et al.

(10) Patent No.: US 10,209,257 B2
(45) Date of Patent: Feb. 19, 2019

(54) SOLID SUPPORT COMPRISING HIV-1 CLADE C ENVELOPE PEPTIDES FOR THE DETECTION OF HIV-1-SPECIFIC ANTIBODIES

(71) Applicant: Biomay AG, Vienna (AT)

(72) Inventors: Rudolf Valenta, Theresienfeld (AT); Daniela Gallerano, Vienna (AT); Elopy N. Sibanda, Harare (ZW)

(73) Assignee: Viravaxx AG, Vienna (AT)

( * ) Notice: Subject to any disclaimer, the term of this patent is extended or adjusted under 35 U.S.C. 154(b) by 50 days.

(21) Appl. No.: 14/775,813

(22) PCT Filed: Mar. 14, 2014

(86) PCT No.: PCT/EP2014/055194
§ 371 (c)(1),
(2) Date: Sep. 14, 2015

(87) PCT Pub. No.: WO2014/140332
PCT Pub. Date: Sep. 18, 2014

(65) Prior Publication Data
US 2016/0011193 A1 Jan. 14, 2016

(30) Foreign Application Priority Data
Mar. 15, 2013 (EP) .................................... 13159417

(51) Int. Cl.
*C07K 14/16* (2006.01)
*G01N 33/569* (2006.01)
*G01N 33/543* (2006.01)
*C07K 14/005* (2006.01)
*C12N 7/00* (2006.01)

(52) U.S. Cl.
CPC ..... *G01N 33/56988* (2013.01); *C07K 14/005* (2013.01); *C07K 14/162* (2013.01); *C12N 7/00* (2013.01); *G01N 33/54366* (2013.01); *C12N 2740/16122* (2013.01); *G01N 2333/16* (2013.01); *G01N 2333/162* (2013.01); *G01N 2469/20* (2013.01)

(58) Field of Classification Search
CPC ....... G01N 33/56988; G01N 33/54366; C07K 14/162; C12N 2740/16122
See application file for complete search history.

(56) References Cited

PUBLICATIONS

Seligman, S., 1994, Serial Deletion Mapping by Competition ELISA Assay: Characterization of a Linear Epitope in the V3 Loop of HIV-1, AIDS Res. Human Retrovir. 10(2):149-156.*
McLain, L., et al., 2001, Different Effects of a Single Amino Acid Substitution on Three Adjacent Epitopes in the gp41 C-terminal Tail of a Neutralizing Antibody Escape Mutant of Human Immunodeficiency Virus Type 1, Arch. Virol. 146:156-166.*
Lynch, R. M., et al., 2011, The B Cell Response is Redundant and Highly Focused on V1V2 during Early Subtype C Infection in a Zambian Seroconverter, J. Virol. 85(2):905-915.*
Murphy, M. K., et al., 2013, Viral Escape form Neutralizing Antibodies in Early Subtype A HIV-1 Infection Drives an Increase in Autologous Neutralization Breadth, PLoS Pathog. 9(2):e1003173, pp. 1-20.*
Alexander, H., et al., Apr. 1992, Altering the antigenicity of proteins, Proc. Natl. Acad. Sci. USA, 89:3352-3356.*
Mitchell, W. M., et al., 1998, Inactivation of a common epitope responsible for the induction of antibody-dependent enhancement of HIV, AIDS 12:147-156.*
Siciliano, S. J., et al., Jan. 1999, A critical site in the core of the CCR5 chemokine receptor required for binding and infectivity of human immunodeficiency virus type 1, J. Biol. Chem. 274(4):1905-1913.*
Mayr, L. M., et al., Jul. 2013, Epitope mapping of conformational V2-specific anti-HIV human monoclonal antibodies reveals an immunodominant site in V2, PLoS One, 8(7):1-9, e70859.*
Casseb et al., "Serotyping HIV-1 with V3 peptides: detection of high avidity antibodies presenting clade-specific reactivity," Braz. J. Med. Biol. Res., (2002) vol. 35, No. 3, pp. 369-375.
Novitsky et al., "Magnitude and Frequency of Cytotoxic T-Lymphocyte Responses: Identification of Immunodominant Regions of Human Immunodeficiency Virus Type 1 Subtype C," J. of Virology, (Oct. 2002), vol. 76, No. 20, pp. 10155-10168.
Riabinina et al., "Evaluation of diagnostic efficiency of the recombinant protein modeling Immunodominant epitope V3 of envelope gp120 for Immunoenzyme detection for HIV-1 infection antibodies," Medline, (2007), pp. 33-36. (English Abstract—Journal Article).
Cardozo et al., "Worldwide Distribution of HIV Type 1 Epitopes Recognized by Human Anti-V3 Monoclonal Antibodies," AIDS Research and Human Retroviruses, (2009), vol. 25, No. 4, pp. 441-451.
Brennan et al., "HIV Global Surveillance: Foundation for Retroviral Discovery and Assay Development," J. of Med. Virology, (2006), vol. 78, pp. S24-S29.

* cited by examiner

*Primary Examiner* — Jeffrey S Parkin
(74) *Attorney, Agent, or Firm* — The Webb Law Firm

(57) ABSTRACT

The present invention relates to a method for detecting and/or quantifying human immunodeficiency virus (HIV) specific antibodies in a sample of a subject comprising the step of determining the presence and/or amount of antibodies binding to a) a peptide consisting of the amino acid sequence AIVCTRPNNNTRKSIRIGPGQVFYT (SEQ ID No. 1), or b) a homolog having at least 70% identity with a peptide of a), or c) a fragment of a peptide of a) or b) consisting of 15 to 24 amino acid residues in said sample.

Figure 1A:
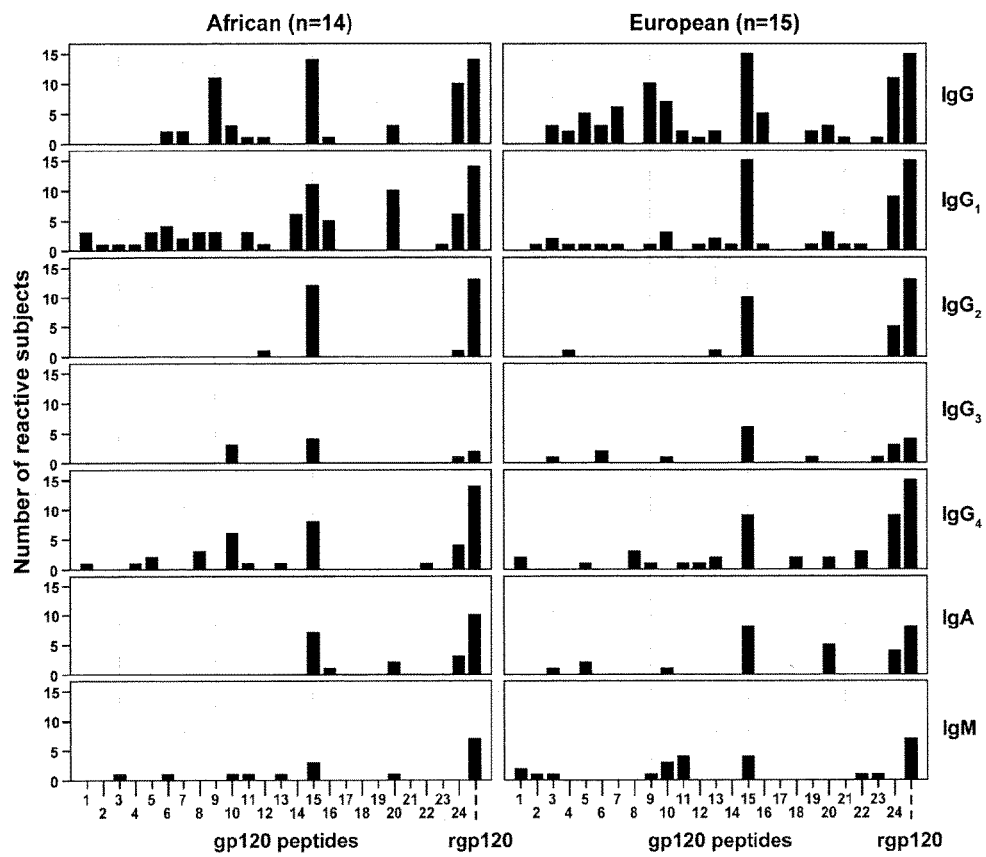

9 Claims, 8 Drawing Sheets
Specification includes a Sequence Listing.

120/15 (aa 292-319)

```
                              300         310
                               |           |
Ref.C.ZA    : AIVCTRPNNNTRKSIRI--GPGQVFYT:
Ref.F2.CMd  : K.N..........--.......A:       88%
Ref.A2.CD   : P.N..........F--....A...:       84%
Ref.C.BR    : E.N..........--....A..A:        84%
Ref.F1.FI   : Q.N..........--....S..A:        84%
Ref.A1.KE   : T.K.I........--....A..A:        80%
Ref.A2.CY   : L.T.I........F--....A...:       80%
Ref.C.IN    : E.M....D.....--....T..A:        80%
Ref.D.TZ    : K.N........G...--....T.F.:      80%
Ref.A1.AU   : N.T.I......V..--....T..A:       76%
Ref.A1.RW   : K.N........T....--....S.HA:     76%
Ref.A1.UG   : T.N........R.V..--....T..A:     76%
Ref.B.FR    : E.N........R...QR...RA.V.:      76%
Ref.B.NL    : E.N...........H.--...RA..A:     76%
Ref.C.ET    : E.T....S....E....--....T..A:    76%
Ref.F1.BR   : Q.N..........R.SL--...R....:    76%
Ref.F1.FR   : Q.N..........HL--....A..A:      76%
Ref.G.BE    : E.N........R.VA.--....A...:     76%
Ref.G.NG    : E.N.I........P.--....A..A:      76%
Ref.H.BE    : Q.N...TG.........--....A..A:    76%
Ref.J.SE    : E............G.HM--.....L.A:    76%
Ref.K.CM    : Q.N...........HM--...KA...:     76%
Ref.B.TH    : E.N....Y...R.TM--...R.Y..:      72%
Ref.F1.BE   : Q.N..........G.HL--....T..A:    72%
Ref.F2.CMa  : I.D.R........G...--....T.FA:    72%
Ref.F2.CMb  : K.N........R..H.--...RA..A:     72%
Ref.F2.CMc  : ..N....T.I..R.M..--...R...A:    72%
Ref.G.PT    : P.T.A..S.......F--....A..A:     72%
Ref.H.BE    : E.T..........G.HF--....A..A:    72%
Ref.J.SE    : E...Y........G.HM--.....L.A:    72%
Ref.K.CD    : E.N....S......H.--...RA..A:     72%
```

Fig. 1C

```
120/15   AIVCTRPNNNTRKSIRIGPGQVFYT   25
Cons C   ---------NTRKSIRIGPGQTFY-   15
                  ************.**
```
Fig. 5A
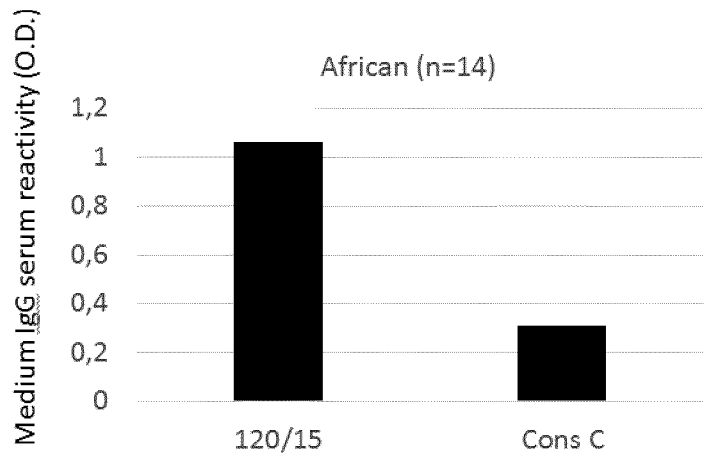
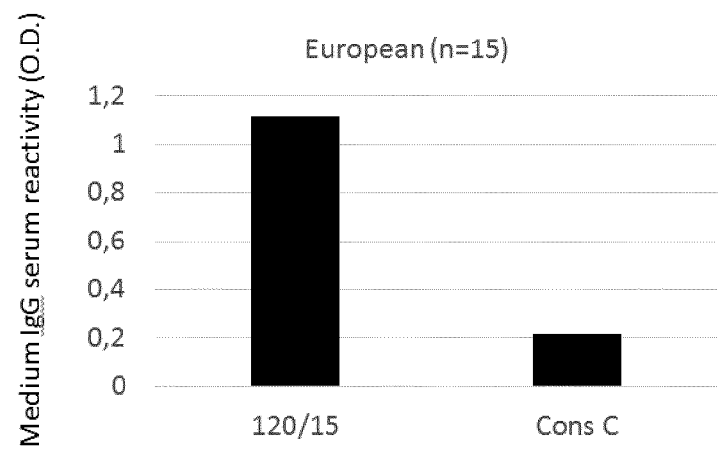
Fig. 5B

SOLID SUPPORT COMPRISING HIV-1 CLADE C ENVELOPE PEPTIDES FOR THE DETECTION OF HIV-1-SPECIFIC ANTIBODIES

CROSS-REFERENCE TO RELATED APPLICATIONS

This application is the United States national phase of International Application No. PCT/EP2014/055194 filed Mar. 14, 2014, and claims priority to European Patent Application No. 13159417.8 filed Mar. 15, 2013, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 159619_ST25.txt. The size of the text file is 23,068 bytes, and the text file was created on Jan. 15, 2018.

The present invention relates to means and methods for diagnosing a human immunodeficiency virus (HIV) infection in a subject.

Human immunodeficiency virus (HIV) is an enveloped RNA virus and represents the etiological agent of the acquired immunodeficiency syndrome (AIDS). In the course of this disease the immune system is progressively destroyed so that already minor microbiological infections may end fatally. It is widely acknowledged that early diagnosis of an HIV infection is important in order to start at an early point in time with the antiviral treatment. This will improve the prognosis of the affected subject (in terms of morbidity and mortality) and reduce the onward transmission of the virus. Furthermore it is also beneficial to monitor the progress of the disease and the effect of the treatment. The detection of antibodies directed to HIV is presumptive evidence of an infection and is usually confirmed by Western blot procedures or by the detection of viral RNA by RT PCR or of viral protein.

In Casseb et al. (Braz J Med Biol Res 35(2002):369-375) synthetic peptides derived from the V3 region of the HIV-1 gp120 protein are disclosed.

Novitsky et al. (J Virol 76(2002):10155-10168) describe the identification of immunodominant regions of HIV-1 subtype C.

In Riabinina et al. (Mol Gen Mikrobiol Virusol 3(2007): 33-36) it was discovered that the peptide corresponding to the V3 region gp120 of HIV-1 subtype C showed the highest immunoreactivity.

Cardozo et al. (AIDS Res Human Retrovir 25(2009):441-450) investigated the worldwide distribution of HIV Type 1 epitopes recognized by human anti-V3 monoclonal antibodies.

Brennan et al. (J Medi Virol 78(2006):S24-S29) is a review article about the difficulties in the development of valuable assays which can be used in detecting HIV infections in individuals.

Difficulties in the detection of antibodies directed to HIV reside in the fact that HIV has a high genetic variability. For instance, HIV type 1 (HIV-1), which is the most common and pathogenic type of the virus, can be divided in several groups and these groups are further divided in various subtypes also known as clades (e.g. group M comprises subtypes A to K). This genetic diversity makes it difficult to provide a diagnostic tool which allows diagnosing HIV more than one subtype in patients having a HIV infection. This means that one test system may be useful to diagnose an HIV subtype A infection but cannot be used to diagnose a HIV subtype D infection.

Therefore it is an object of the present invention to provide methods and means to diagnose HIV infections of more than one subtype.

The present invention relates to a method for diagnosing a human immunodeficiency virus (HIV) infection in a subject comprising the steps of determining the presence of antibodies binding to a) a peptide consisting of the amino acid sequence AIVCTRPNNNTRKSIRIGPGQVFYT (SEQ ID No. 1), or b) a homolog having at least 70% identity with a peptide of a), or c) a fragment of a peptide of a) or b) consisting of 15 to 24 amino acid residues, in a sample of the subject, and diagnosing an HIV infection in said patient when the presence of such antibodies in said sample is determined or diagnosing no HIV infection in said patient when the absence of such antibodies in said sample is determined.

It surprisingly turned out that peptide fragments and homologs thereof derived from the envelope protein gp120 of HIV subtype C can be used to diagnose HIV infections of more than one, preferably of more than two, preferably of more than three, more preferably of more than four, more preferably of more than five, more preferably of more than six, more preferably of more than seven, even more preferably of more than eight, HIV subtypes since antibodies directed to gp120 of all of these subtypes and obtainable from subjects having a HIV infection bind to a peptide consisting of the amino acid sequence AIVCTRPNNNTRKSIRIGPGQVFYT (SEQ ID No. 1) or a homolog or a fragment thereof consisting of 15 to 24 amino acid residues. Hence, the method of the present invention allows to diagnose HIV infections of HIV subtypes A, B, C, D, F, G, H, J and/or K, whereby the diagnosis of HIV subtypes B and C is most preferred.

Figure 4:
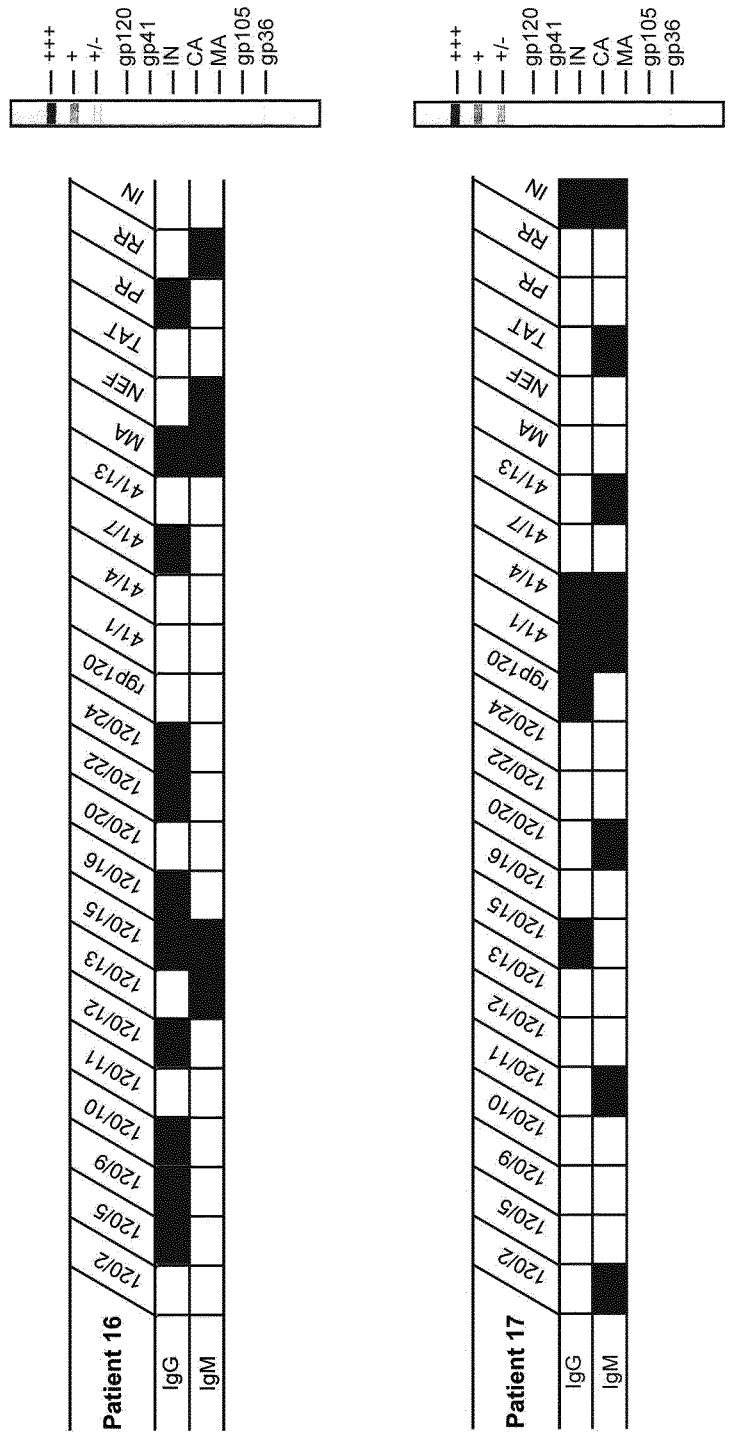

The method of the present invention allows diagnosing an HIV infection and to detect antibodies in an individual although other established conventional assays fail (see examples and FIG. 4). This is a rather surprising finding since it shows that the use of methods known in the art for the diagnosis of HIV infections in individuals is not really fully reliable.

The method of the present invention can also be used to diagnose that a subject has no HIV infection if the presence of the aforementioned antibodies cannot be determined in a sample of the subject.

Suitable fragments of AIVCTRPNNNTRKSIRIGPGQVFYT (SEQ ID No. 1) and/or LLGLWGCSGKLICTTAVHWNSSWSN (SEQ ID No. 2) or a homolog having at least 70% identity to SEQ ID ID No. 1 and/or 2 to be used in the present invention consist of 15 to 24, preferably 16 to 24, amino acid residues of SEQ ID No. 1 and/or 2, respectively. These fragments may consist of amino acid residues 1 to 23, 1 to 22, 1 to 21, 1 to 20, 1 to 19, 1 to 18, 1 to 17, 1 to 16, 1 to 15, 2 to 24, 2 to 23, 2 to 22, 2 to 21, 2 to 20, 2 to 19, 2 to 18, 2 to 17, 2 to 16, 3 to 24, 3 to 23, 3 to 22, 3 to 21, 3 to 20, 3 to 19, 3 to 18, 3 to 17, 4 to 24, 4 to 23, 4 to 22, 4 to 21, 4 to 20, 4 to 19, 4 to 18, 5 to 24, 5 to 23, 5 to 22, 5 to 21, 5 to 20, 5 to 19, 6 to 24, 6 to 23, 6 to 22, 6 to 21, 6 to 20, 7 to 24, 7 to 23, 7 to 22, 7 to 21, 8 to 24, 8 to 23, 8 to 22, 9 to 24, 9 to 23, 2 to 25, 3 to 25, 4 to 25, 5 to 25, 6 to 25, 7 to 25, 8 to 25, 9 to 25 or 10 to 25 of SEQ ID No. 1 and/or 2.

The presence of antibodies in a sample can be determined using methods known in the art (e.g. immunoassays such as ELISA). For instance, one or more of the peptides of the present invention can be immobilised on a solid support. The solid support is then contacted with the sample comprising antibodies of the subject who is suspected to have an HIV infection. Antibodies able to bind to the peptides of the present invention will be immobilised on the solid support. These immobilised antibodies can be detected by using other antibodies, for instance, antibodies which are directed to one or more of the antibody isotypes IgA, IgG, IgG1, IgG2, IgG3, IgG4 and/or IgM.

The presence of antibodies directed to HIV-derived peptides and/or polypeptides in a sample of a subject indicates that said subject has an HIV infection. The absence of antibodies directed to HIV-derived peptides and/or polypeptides in a sample of a subject indicates that said subject has no HIV infection. IgM antibodies occur in higher amounts during acute infection, and their presence in human samples (e.g. serum, plasma) is used to diagnose early infections. IgG antibodies are low at early infection stages, but occur in patients during established infections. Most antibody-based HIV-diagnostic tests detect the presence of HIV-specific IgG in human samples (e.g. serum, plasma). IgA is a marker of mucosal immunity and can be detected in human secretes such as saliva, tears, etc., as well as in serum. Such antibodies are known to a person skilled in the art.

In order to facilitate the immobilisation of the polypeptides and peptides of the present invention on a solid support it is advantageous to add to the C- and/or N-terminal end of said polypeptides and peptides cysteine residues or other moieties (e.g. linkers or carrier proteins, biotin, nucleic acids). This allows a facilitated attachment of the peptides and/or polypeptides on a solid support. Methods and means to attach peptidic molecules on a solid support are well known to a person skilled in the art.

"Human immunodeficiency virus (HIV)", as used herein, refers to the HIV type 1 (HIV-1).

As used herein the term "subject" can be used interchangeably with "human individual", "human" or "individual".

A "homolog having at least 70% identity with a peptide" or "homolog", as used herein, refers to peptides which have at least 70%, preferably at least 75% identity, more preferably at least 80% identity, even more preferably at least 85% or 90% or 95% identity, with a peptide consisting of an amino acid sequence as defined herein (any one of SEQ ID Nos. 1 to 41), e.g. consisting of the amino acid sequence AIVCTRPNNNTRKSIRIGPGQVFYT (SEQ ID No. 1) or LLGLWGCSGKLICTTAVHWNSSWSN (SEQ ID No. 2). Sequence identity is determined by BLAST alignment (Altschul S F et al J. Mol. Biol. 215(1990):403-410) using the BLOSUM62 matrix, a gap existence penalty of 11, and a gap extension penalty of 1.

"Homologs", as used herein, are to be considered as "variants" of the peptides of the present invention which have an amino acid sequence that differs by one or more amino acid residues from another related peptide having any one of the amino acid sequences SEQ ID No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41. The "variant" or "homolog" may have "conservative" amino acid changes, wherein a substituted amino acid has similar structural or chemical properties. One type of conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalaninetyrosine, lysine-arginine, alanine-valine, and asparagineglutamine. More rarely, a "variant" or "homolog" may have "nonconservative" changes (for example, replacement of a glycine with a tryptophan).

The "homologs" or "variants" of the present invention may have at least one, at least two, at least three, at least four, at least five, at least six, or seven amino acid change (substitution or deletion) compared to a peptide having any one of the amino acid sequences SEQ ID No. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41. The "homologs" or "variants" of the present invention may have a maximum number of one, two, three, four, five, six or seven amino acid changes.

According to a preferred embodiment of the present invention the fragment of the peptides disclosed herein (SEQ ID No. 1 to 41) consist of 15 to 24, preferably 16 to 24, 17 to 24, 18 to 24, 19 to 24, 20 to 24, 21 to 24, 22 to 24, 23 to 24, 16 to 23, 17 to 23, 18 to 23, 19 to 23, 20 to 23, 21 to 23, 22 to 23, 16 to 22, 17 to 22, 18 to 22, 19 to 22, 20 to 22, 21 to 22, 16 to 21, 17 to 21, 18 to 21, 19 to 21, 20 to 21, 16 to 20, 17 to 20, 18 to 20, 19 to 20, 16 to 19, 17 to 19, 18 to 19, 16 to 18 or 17 to 18 amino acid residues, in particular of 15, 16, 17, 18, 19, 20, 21, 22, 23 or 24 amino acid residues.

Another aspect of the present invention relates to a method for detecting and/or quantifying human immunodeficiency virus (HIV) specific antibodies in a sample of a subject comprising the step of determining the presence and/or amount of antibodies binding to a) a peptide consisting of the amino acid sequence AIVCTRPNNNTRKSIRIGPGQVFYT (SEQ ID No. 1), or b) a homolog having at least 70% identity with a peptide of a), or c) a fragment of a peptide of a) or b) consisting of 15 to 24 amino acid residues in said sample.

The presence of antibodies directed to HIV-derived peptides and/or polypeptides in a sample of a subject indicates that said subject has an HIV infection. The absence of antibodies directed to HIV-derived peptides and/or polypeptides in a sample of a subject indicates that said subject has no HIV infection.

A further aspect of the present invention relates to a method for detecting and/or quantifying human immunodeficiency virus (HIV) specific antibodies in a sample of a subject comprising the step of determining the presence and/or amount of antibodies binding to a) a peptide consisting of the amino acid sequence AIVCTRPNNNTRKSIRIGPGQVFYT (SEQ ID No. 1), or b) a homolog having at least 70% identity with a peptide of a), or c) a fragment of a peptide of a) or b) consisting of 15 to 24 amino acid residues in said sample.

Yet another aspect of the present invention relates to a method for monitoring the progress of a human immunodeficiency virus (HIV) infection in a subject comprising the step of determining the amount of antibodies binding to a) a peptide consisting of the amino acid sequence AIVCTRPNNNTRKSIRIGPGQVFYT (SEQ ID No. 1), or b) a homolog having at least 70% identity with a peptide of a), or c) a fragment of a peptide of a) or b) consisting of 15 to 24 amino acid residues in said sample.

Another aspect of the present invention relates to a method for monitoring the effects of treatment of a subject with an anti-HIV agent comprising the steps of:

(i) determining the amount of antibodies binding to
 a) a peptide consisting of the amino acid sequence AIVCTRPNNNTRKSIRIGPGQVFYT (SEQ ID No. 1), or
 b) a homolog having at least 70% identity with a peptide of a), or
 c) a fragment of a peptide of a) or b) consisting of 15 to 24 amino acid residues in a sample of the subject prior to administration of said anti-HIV agent, (ii) determining the amount of antibodies binding to
 a) a peptide consisting of the amino acid sequence AIVCTRPNNNTRKSIRIGPGQVFYT (SEQ ID No. 1), or
 b) a homolog having at least 70% identity with a peptide of a), or
 c) a fragment of a peptide of a) or b) consisting of 15 to 24 amino acid residues in a sample of the subject in one or more post-administration samples of said subject, (iii) comparing the amount of the determined antibodies in the sample of the subject prior to administration of said anti-HIV agent with the amount of the determined antibodies in the one or more post administration sample or samples, and (iv) determining whether said anti-HIV agent influences the levels and/or isotypes of HIV-specific antibodies in said subject.

The peptides of the present invention can also be used to determine the presence of HIV specific antibodies in patients who are treated with an anti-HIV agent (e.g. antiretroviral agents). This allows to monitor and to determine whether an anti-HIV agent influences the levels and/or isotypes of HIV-specific antibodies in said subject. For instance, if the amount of HIV specific antibodies determined in step (ii) is lower (e.g. at least 10%, at least 20%, at least 50%, at least 80%) compared to step (i) the anti-HIV agent may positively influence the course of the disease because it may indicate that the HIV load is reduced. If, however, the amount of HIV specific antibodies determined in step (ii) is higher (e.g. at least 10%, at least 20%, at least 50%, at least 80%, at least 100%) compared to step (i) the anti-HIV agent may have no influence on the course of the disease and will most probably not be considered as being useful in the treatment of HIV infections.

In order to enhance the informative value of the methods of the present invention it is advantageous to determine further the presence of other antibodies which are able to bind to other polypeptides encoded by the HIV genome or to peptidic fragments thereof (e.g. to a peptide consisting of any one of SEQ ID Nos. 1 to 41).

According to a preferred embodiment of the present invention the presence and/or amount of antibodies binding to a) a peptide consisting of the amino acid sequence LLGLWGCSGKLICTTAVHWNSSWSN (SEQ ID No. 2), b) a homolog having at least 70% identity with a peptide of a), or c) a fragment of a peptide of a) or b) consisting of 15 to 24 amino acid residues in a sample of the subject is further determined.

The peptide having amino acid sequence LLGLWGCSGKLICTTAVHWNSSWSN (SEQ ID No. 2) is derived from the HIV polypeptide gp41 (subtype C) which is part of the HIV envelope protein complex. Surprisingly, HIV infected subjects produce a significant amount of antibodies binding to this peptide or fragments thereof. Therefore the additional detection and/or quantification of such antibodies allows an even more powerful diagnosis of HIV infected subjects.

It is an unexpected finding that also peptide fragments derived from the envelope protein gp41 of HIV subtype C can be used to diagnose HIV infections of more than one, preferably of more than two, preferably of more than three, more preferably of more than four, more preferably of more than five, more preferably of more than six, more preferably of more than seven, even more preferably of more than eight, HIV subtypes since antibodies directed to gp41 of all of these subtypes and obtainable from subjects having an HIV infection bind to a peptide consisting of the amino acid sequence LLGLWGCSGKLICTTAVHWNSSWSN (SEQ ID No. 2) or a homolog or a fragment thereof consisting of 15 to 24 amino acid residues. Hence, the method of the present invention allows to diagnose HIV infections of HIV subtypes A, B, C, D, F, G, H, J and/or K, whereby the diagnosis of HIV subtypes B and C is most preferred.

Therefore a further aspect of the present invention relates to a method for diagnosing a human immunodeficiency virus (HIV) infection in a subject comprising the step of determining the presence of antibodies binding to a) a peptide consisting of the amino acid sequence LLGLWGCSGKLICTTAVHWNSSWSN (SEQ ID No. 2), or b) a homolog having at least 70% identity with a peptide of a), or c) a fragment of a peptide of a) or b) consisting of 15 to 24 amino acid residues in a sample of the subject, and diagnosing an HIV infection in said patient when the presence of such antibodies in said sample is determined or diagnosing no HIV infection in said patient when the absence of such antibodies in said sample is determined. LLGLWGCSGKLICTTAVHWNSSWSN (SEQ ID No. 2) as well as its homologs and fragments thereof can also be used—according to a further aspect of the present invention—in a method for monitoring the effectiveness of treatment to a subject with an anti-HIV agent as defined above. Such methods can also be used in combination with a step of determining the presence of antibodies binding to a peptide consisting of the amino acid sequence AIVCTRPNNNTRKSIRIGPGQVFYT (SEQ ID No. 1) or a homolog or a fragment thereof consisting of 15 to 24 amino acid residues as defined above.

Another aspect of the present invention relates to a method for detecting and/or quantifying human immunodeficiency virus (HIV) specific antibodies in a sample of a subject comprising the step of determining the presence and/or amount of antibodies binding to a) a peptide consisting of the amino acid sequence LLGLWGCSGKLICTTAVHWNSSWSN (SEQ ID No. 2), or b) a homolog having at least 70% identity with a peptide of a), or c) a fragment of a peptide of a) or b) consisting of 15 to 24 amino acid residues in said sample.

A further aspect of the present invention relates to a method for detecting and/or quantifying human immunodeficiency virus (HIV) specific antibodies in a sample of a subject comprising the step of determining the presence and/or amount of antibodies binding to
- a) a peptide consisting of the amino acid sequence LLGLWGCSGKLICTTAVHWNSSWSN (SEQ ID No. 2), or
- b) a homolog having at least 70% identity with a peptide of a), or
- c) a fragment of a peptide of a) or b) consisting of 15 to 24 amino acid residues in said sample.

Yet another aspect of the present invention relates to a method for monitoring the progress of a human immunodeficiency virus (HIV) infection in a subject comprising the step of determining the amount of antibodies binding to
- a) a peptide consisting of the amino acid sequence LLGLWGCSGKLICTTAVHWNSSWSN (SEQ ID No. 2), or
- b) a homolog having at least 70% identity with a peptide of a), or
- c) a fragment of a peptide of a) or b) consisting of 15 to 24 amino acid residues in said sample.

Another aspect of the present invention relates to a method for monitoring the effects of treatment of a subject with an anti-HIV agent comprising the steps of:
- (i) determining the amount of antibodies binding to
  - a) a peptide consisting of the amino acid sequence LLGLWGCSGKLICTTAVHWNSSWSN (SEQ ID No. 2), or
  - b) a homolog having at least 70% identity with a peptide of a), or
  - c) a fragment of a peptide of a) or b) consisting of 15 to 24 amino acid residues in a sample of the subject prior to administration of said anti-HIV agent,
- (ii) determining the amount of antibodies binding to
  - a) a peptide consisting of the amino acid sequence LLGLWGCSGKLICTTAVHWNSSWSN (SEQ ID No. 2), or
  - b) a homolog having at least 70% identity with a peptide of a), or
  - c) a fragment of a peptide of a) or b) consisting of 15 to 24 amino acid residues in a sample of the subject in one or more post-administration samples of said subject,
- (iii) comparing the amount of the determined antibodies in the sample of the subject prior to administration of said anti-HIV agent with the amount of the determined antibodies in the one or more post administration sample or samples, and
- (iv) determining whether said anti-HIV agent influences the levels and/or isotypes of HIV-specific antibodies in said subject.

According to a further preferred embodiment of the present invention the presence and/or amount of antibodies binding to
- a) a peptide consisting of the amino acid sequence NALFYRSDIVPLEKNSSEYILINCN (SEQ ID No. 3), or
- b) a homolog having at least 70% identity with a peptide of a), or
- c) a fragment of a peptide of a) or b) consisting of 15 to 24 amino acid residues in a sample of the individual is further determined.

The peptide having the amino acid sequence NALFYRSDIVPLEKNSSEYILINCN (SEQ ID No. 3) is derived from the HIV polypeptide gp120 (subtype C).

According to a preferred embodiment of the present invention the presence and/or amount of antibodies binding to
- a) a peptide consisting of the amino acid sequence GIKQLQARVLAIERYLKDQQLLGLW (SEQ ID No. 4), or
- b) a homolog having at least 70% identity with a peptide of a), or
- c) a fragment of a peptide of a) or b) consisting of 15 to 24 amino acid residues in a sample of the individual is further determined.

The peptide having the amino acid sequence GIKQLQARVLAIERYLKDQQLLGLW (SEQ ID No. 4) is derived from the HIV polypeptide gp41 (subtype C).

The fragments of all of these peptides or homologs having at least 70% identity to said peptides may consist of amino acid residues 1 to 24, 1 to 23, 1 to 22, 1 to 21, 1 to 20, 1 to 19, 1 to 18, 1 to 17, 1 to 16, 1 to 15, 2 to 24, 2 to 23, 2 to 22, 2 to 21, 2 to 20, 2 to 19, 2 to 18, 2 to 17, 2 to 16, 3 to 24, 3 to 23, 3 to 22, 3 to 21, 3 to 20, 3 to 19, 3 to 18, 3 to 17, 4 to 24, 4 to 23, 4 to 22, 4 to 21, 4 to 20, 4 to 19, 4 to 18, 5 to 24, 5 to 23, 5 to 22, 5 to 21, 5 to 20, 5 to 19, 6 to 24, 6 to 23, 6 to 22, 6 to 21, 6 to 20, 7 to 24, 7 to 23, 7 to 22, 7 to 21, 8 to 24, 8 to 23, 8 to 22, 9 to 24, 9 to 23, 2 to 25, 3 to 25, 4 to 25, 5 to 25, 6 to 25, 7 to 25, 8 to 25, 9 to 25 or 10 to 25 of SEQ ID No. 1 to 41.

According to a particularly preferred embodiment of the present invention the presence and/or amount of antibodies binding to
- a) a peptide consisting of the amino acid sequence WRSELYKYKVVEIKPLGIAPTKAKRRVVEREKR (SEQ ID No. 5), or
- b) a homolog having at least 70% identity with a peptide of a), or
- c) a fragment of a peptide of a) or b) consisting of 15 to 32 amino acid residues in a sample of the individual is further determined.

The peptide having the amino acid sequence WRSELYKYKVVEIKPLGIAPTKAKRRVVEREKR (SEQ ID No. 5) is derived from the HIV polypeptide gp120 (subtype C).

The fragments of this peptide or a homolog having at least 70% identity to said peptide may consist of amino acid residues 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 2 to 32, 2 to 31, 2 to 30, 2 to 29, 2 to 28, 2 to 27, 2 to 26, 2 to 25, 2 to 24, 2 to 23, 2 to 22, 2 to 21, 2 to 20, 2 to 19, 2 to 18, 2 to 17, 2 to 16, 3 to 32, 3 to 31, 3 to 30, 3 to 29, 3 to 28, 3 to 27, 3 to 26, 3 to 25, 3 to 24, 3 to 23, 3 to 22, 3 to 21, 3 to 20, 3 to 19, 3 to 18, 3 to 17, 4 to 32, 4 to 31, 4 to 30, 4 to 29, 4 to 28, 4 to 27, 4 to 26, 4 to 25, 4 to 24, 4 to 23, 4 to 22, 4 to 21, 4 to 20, 4 to 19, 4 to 18, 5 to 32, 5 to 31, 5 to 30, 5 to 29, 5 to 28, 5 to 27, 5 to 26, 5 to 25, 5 to 24, 5 to 23, 5 to 22, 5 to 21, 5 to 20, 5 to 19, 6 to 32, 6 to 31, 6 to 30, 6 to 29, 6 to 28, 6 to 27, 6 to 26, 6 to 25, 6 to 24, 6 to 23, 6 to 22, 6 to 21, 6 to 20, 7 to 32, 7 to 31, 7 to 30, 7 to 29, 7 to 28, 7 to 27, 7 to 26, 7 to 25, 7 to 24, 7 to 23, 7 to 22, 7 to 21, 8 to 32, 8 to 31, 8 to 30, 8 to 29, 8 to 28, 8 to 27, 8 to 26, 8 to 25, 8 to 24, 8 to 23, 8 to 22, 9 to 32, 9 to 31, 9 to 30, 9 to 29, 9 to 28, 9 to 27, 9 to 26, 9 to 25, 9 to 24, 9 to 23, 10 to 32, 10 to 31, 10 to 30, 10 to 29, 10 to 28, 10 to 27, 10 to 26, 10 to 25, 10 to 24, 11 to 32, 11 to 31, 11 to 30, 11 to 29, 11 to 28, 11 to 27, 11 to 26, 11 to 25, 12 to 32, 12 to 31, 12 to 30, 12 to 29, 12 to 28, 12 to 27, 12 to 26, 13 to 32, 13 to 31, 13 to 30, 13 to 29, 13 to 28, 13 to 27, 14 to 32, 14 to 31, 14 to 30, 14 to 29, 14 to 28, 15 to 32, 15 to 31, 15 to 30, 15 to 29, 16 to 32, 16 to 31, 16 to 30, 17 to 32, 17 to 31, 2 to 33, 3 to 33, 4 to 33, 5 to 33, 6 to 33, 7 to 33, 8 to 33, 9 to 33, 10 to 33, 11 to 33, 12 to 33, 13 to 33, 14 to 33, 15 to 33, 16 to 33, 17 to 33, 18 to 33 or 19 to 33 of SEQ ID No. 5.

In some preferred embodiments the methods of the present invention involve the determination of the presence and/or amount of antibodies binding to more than one peptide, homolog or fragment as defined herein. Preferred combinations include the following peptides and its respective homologs and fragments as defined above: SEQ ID No. 1 with SEQ ID No. 2; SEQ ID No. 1 with SEQ ID No. 3; SEQ ID No. 1 with SEQ ID No. 4; SEQ ID No. 1 with SEQ ID No. 5; SEQ ID No. 2 with SEQ ID No. 3; SEQ ID No. 2 with SEQ ID No. 4; SEQ ID No. 2 with SEQ ID No. 5; SEQ ID No. 1 with SEQ ID No. 2 and SEQ ID No. 3; SEQ ID No. 1 with SEQ ID No. 2 and SEQ ID No. 4; SEQ ID No. 1 with SEQ ID No. 2 and SEQ ID No. 5; SEQ ID No. 2 with SEQ ID No. 3 and SEQ ID No. 4; SEQ ID No. 2 with SEQ ID No. 3 and SEQ ID No. 5; SEQ ID No. 1 with SEQ ID No. 2, SEQ ID No. 3 and SEQ ID No. 4; SEQ ID No. 1 with SEQ ID No. 2, SEQ ID No. 3 and SEQ ID No. 5; SEQ ID No. 2 with SEQ ID No. 3, SEQ ID No. 4 and SEQ ID No. 5; SEQ ID No. 1 with SEQ ID No. 2, SEQ ID No. 3, SEQ ID No. 4 and SEQ ID No. 5. Of course it is also possible to combine this combinations with at least one, two, three, five, six, seven, eight, nine or ten of the peptides having SEQ ID No. 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41.

According to a further preferred embodiment of the present invention the presence and/or amount of antibodies binding to HIV capsid protein p24 in a sample of the individual is further determined.

According to a particularly preferred embodiment of the present invention the presence and/or amount of antibodies binding to at least one polypeptide selected from the group consisting of HIV integrase, HIV reverse transcriptase+ RNAse H, HIV protease and HIV matrix protein p17 in a sample of the individual is further determined.

The presence and/or amount of antibodies binding to a peptide or polypeptide in a sample can be determined using various methods. It is particularly preferred to use a method selected from the group consisting of enzyme-linked immunosorbent assay (ELISA), radioimmune assay (RIA), Western blot assay, dot blot assay, bead assay, peptide array and polypeptide array.

According to a particularly preferred embodiment of the present invention the sample of the subject is a sample selected from the group consisting of blood sample, serum sample, plasma sample, saliva, tears, urine, nose secret, genital secretion, stool and breast milk, whereby blood, serum or plasma samples are particularly preferred.

The sample taken from a subject suspected or known of having an HIV infection comprises a pool of antibodies of various subtypes directed to various epitopes of the polypeptides and peptides of the HIV. Therefore, according to a preferred embodiment of the present invention the antibodies to be determined and/or quantified are selected from the group consisting of IgG, IgG1, IgG2, IgG3, IgG4, IgA and IgM, wherein IgG and IgM are particularly preferred.

The presence and/or the amount of antibodies in a sample of a subject can be determined by using one single peptide or polypeptide as defined herein or by using more than one, preferably more than two, more preferably more than three, even more preferably more than four, of said peptides or polypeptides. This allows determining simultaneously the presence and/or amount of antibodies binding to different antigens and epitopes.

The peptides and proteins of the present invention can be added in liquid phase to a serum of an individual in order to pre-adsorb the antibodies comprised in the serum which are specific for or bind to at least one (preferably at least two, three, four, five, six, ten or even all) peptide and/or protein disclosed herein followed by the subsequent binding of the remaining free antibodies against the complete glycosylated antigens of the virus in order to determine the epitope specificity and portion of antibodies directed towards the peptide, sum of peptides or sum of peptides and proteins to obtain additional diagnostic and or prognostic information.

Another aspect of the present invention relates to a peptide consisting of the amino acid sequence selected from the group consisting of AIVCTRPNNNTRKSIRIGPGQV-FYT (SEQ ID No. 1), LLGLWGCSGKLICTTAVHWNSS-WSN (SEQ ID No. 2), RVRGILRNWPQWWIWGILGFW-MIII (SEQ ID No. 6), WMIIICRGEENSWVTVYYGVPVWTE (SEQ ID No. 7), PVWTEAKTTLFCASDAKAYEKEVHN (SEQ ID No. 8), KEVHNVWATHACVPTDPSPQELVLE (SEQ ID No. 9), ELVLENVTESFNMWENDMVDQMHED (SEQ ID No. 10), QMHEDIIGLWDESLKPCVKLTPLCV (SEQ ID No. 11), TPLCVTLNCNTTSHNNSSPSPMTNC (SEQ ID No. 12), PMTNCSFNATTELRDKTQKVNALFY (SEQ ID No. 13), NALFYRSDIVPLEKNSSEYILINCN (SEQ ID No. 3), LINCNTSTITQACPKVSFDPIPIHY (SEQ ID No. 14), IPI-HYCAPAGYAILKCNNKTFNGTG (SEQ ID No. 15), FNGTGPCSNVSTVQCTHGIKPVVST (SEQ ID No. 16), PVVSTQLLLNGSLAEGEIIIRSENL (SEQ ID No. 17), RSENLTDNAKTIIVHLNKSVAIVCT (SEQ ID No. 18), QVFYTNEIIGNIRQAHCNISRELWN (SEQ ID No. 19), RELWNNTLEQVKKKLKEHFQNKTIE (SEQ ID No. 20), NKTIEFQPPAGGDLEVTTHSFNCRG (SEQ ID No. 21), FNCRGEFFYCNTSNLFNITASNASD (SEQ ID No. 22), SNASDANNNTITLPCKIKQIINMWQ (SEQ ID No. 23), INMWQEVGRAMYAPPIAGNITCNSS (SEQ ID No. 24), TCNSSITGLLLTRDGGNNNDTGNNN (SEQ ID No. 25), TGNNNDTEIFRPGGGNMKDNWRSEL (SEQ ID No. 26), AVGLGAVLLGFLGTAGSTMGAASIT (SEQ ID No. 27), AASITLTVQARQLLSGIVQQQSNLL (SEQ ID No. 28), QSNLLRAIEAQQHMLQLTVWGIKQL (SEQ ID No. 29), GIKQLQARVLAIERYLKDQQLLGLW (SEQ ID No. 4), SSWSNKSQDYIWGNMTWMQWDREIN (SEQ ID No. 30), DREINNYTDIIYTLLEESQSQQEKN (SEQ ID No. 31), QQEKNEKDLLALDSWNNLWNWFSIT (SEQ ID No. 32), WFSITKWLWYIKIFIMIVGGLIGLR (SEQ ID No. 33), LIGLRIILGVLSIVKRVRQGYSPLS (SEQ ID No. 34), YSPLSFQTLPPNPRGPDRLRGIEEE (SEQ ID No. 35), GIEEEGGEQDKDRSIRLVSGFLALV (SEQ ID No. 36), FLALVWEDLRSLCLFSYHRLRDFIL (SEQ ID No. 37), RDFILIAGRAAELLGRSSLRGLQTG (SEQ ID No. 38), GLQTGWQALKYLGSLVQYWGLELKK (SEQ ID No. 39) and LELKKSAINLFDTTAIVVAEGTDRL (SEQ ID No. 40) or a fragment thereof consisting of 15 to 24 amino acid residues or consisting of the amino acid sequence WRSELYKYKVVEIKPLGIAPTKAKRRVVER-EKR (SEQ ID No. 5) or a fragment thereof consisting of 15 to 32 amino acid residues or consisting of the amino acid sequence GTDRLIEGLQGIGRAIYNIPRRIRQGFEAALL (SEQ ID No. 41) or a fragment thereof consisting of 15 to 31 amino acid residues.

The peptides of the present invention can be synthetically produced by chemical synthesis methods which are well known in the art. Alternatively, the peptides may be coupled to a polypeptide carrier (e.g. Keyhole limpet hemocyanin) to augment their stability. Furthermore, they may be produced as recombinant fusion proteins together with a carrier molecule or coupled via known interactions (Biotin-Streptavidin-Avidin).

The polypeptides can be produced in a microorganism and then be isolated and if desired, further purified. The polypeptides can be produced in microorganisms such as bacteria, yeast or fungi, in eukaryote cells such as a mammalian or an insect cell, or in a recombinant virus vector such as adenovirus, poxvirus, herpesvirus, Simliki forest virus, baculovirus, bacteriophage, sindbis virus or sendai virus. Suitable bacteria for producing the compound/peptide include *E. coli, B. subtilis* or any other bacterium that is capable of expressing peptides. Suitable yeast types for expressing said compound/peptide include *Saccharomyces cerevisiae, Schizosaccharomyces pombe, Candida, Pichia pastoris* or any other yeast capable of expressing peptides. Corresponding methods are well known in the art. Also methods for isolating and purifying recombinantly produced polypeptides are well known in the art and include e.g. as gel filtration, affinity chromatography, ion exchange chromatography etc.

To facilitate the isolation of the polypeptide, a fusion polypeptide may be made wherein the polypeptide is translationally fused (covalently linked) to a heterologous peptide or polypeptide which enables isolation by affinity chromatography. Typical heterologous peptides or polypeptides are His-Tag (e.g. His6; 6 histidine residues), GST-Tag (Glutathione-S-transferase) etc. The fusion polypeptide facilitates not only the purification of the peptide but may also prevent the degradation of said peptide during purification. If it is desired to remove the heterologous polypeptide after purification, the fusion polypeptide may comprise a cleavage site at the junction between the polypeptide and the heterologous peptide or polypeptide. The cleavage site consists of an amino acid sequence that is cleaved with an enzyme specific for the amino acid sequence at the site (e.g. proteases).

The polypeptides used in the methods of the present invention (such as HIV capsid protein p24, HIV integrase, HIV reverse transcriptase+RNAse H, HIV protease and HIV matrix protein p17) are preferably recombinantly produced using methods known in the art.

Another aspect of the present invention relates to a solid support comprising one or more peptides as disclosed herein, wherein the solid support comprises a) a peptide consisting of the amino acid sequence AIVCTRPNNNTRKSIRIGPGQVFYT (SEQ ID No. 1), or b) a homolog having at least 70% identity with a peptide of a), or c) a fragment of a peptide of a) or b) consisting of 15 to 24 amino acid residues immobilised thereon.

An alternative aspect of the present invention relates to a solid support comprising one or more peptides as disclosed herein, said solid support comprising a) a peptide consisting of the amino acid sequence LLGLWGCSGKLICTTAVHWNSSWSN (SEQ ID No. 2), or b) a homolog having at least 70% identity with a peptide of a), or c) a fragment of a peptide of a) or b) consisting of 15 to 24 amino acid residues immobilised thereon.

An alternative aspect of the present invention relates to a solid support comprising one or more peptides as disclosed herein for determining the presence or absence and/or the amount of antibodies binding to the human immunodeficiency virus (HIV) in sample, said solid support comprising a) a peptide consisting of the amino acid sequence LLGLWGCSGKLICTTAVHWNSSWSN (SEQ ID No. 2), or b) a homolog having at least 70% identity with a peptide of a), or c) a fragment of a peptide of a) or b) consisting of 15 to 24 amino acid residues immobilised thereon.

These solid supports can be used in the methods of the present invention, e.g., in particular for determining the presence or absence and/or the amount of antibodies binding to the human immunodeficiency virus (HIV) in a sample, diagnosing a human immunodeficiency virus (HIV) infection in a subject, monitoring the course and progress of a human immunodeficiency virus (HIV) infection in a subject monitoring the effects of treatment on a subject with an anti-HIV agent or any other method involving the determination of antibodies binding to HIV.

A solid support of the present invention can be selected from the group consisting of glass, polystyrene, PVDF membrane, nylon, nitrocellulose, sepharose and agarose.

The immobilisation onto the solid support of the peptides and polypeptides of the present invention may be achieved by immobilising them directly onto the solid support. Alternatively the peptides may be modified C- and/or N-terminally with a cysteine residue or other known moieties which allow immobilising molecules on a solid support. Such immobilisation may be effected by covalent or non-covalent binding. Such covalent or non-covalent binding onto a solid support may be performed by methods and by use of agents well known in the art.

According to a preferred embodiment of the present invention a peptide consisting of the amino acid sequence LLGLWGCSGKLICTTAVHWNSSWSN (SEQ ID No. 2) or AIVCTRPNNNTRKSIRIGPGQVFYT (SEQ ID No. 1), respectively, or a homolog as defined above or a fragment thereof consisting of 15 to 24 amino acid residues is further immobilised on said solid support.

According to another preferred embodiment of the present invention a) a peptide consisting of the amino acid sequence NALFYRSDIVPLEKNSSEYILINCN (SEQ ID No. 3), or b) a homolog having at least 70% identity with a peptide of a), or c) a fragment of a peptide of a) or b) consisting of 15 to 24 amino acid residues is further immobilised thereon.

According to a particularly preferred embodiment of the present invention a) a peptide consisting of the amino acid sequence GIKQLQARVLAIERYLKDQQLLGLW (SEQ ID No. 4), or b) a homolog having at least 70% identity with a peptide of a), or c) a fragment of a peptide of a) or b) consisting of 15 to 24 amino acid residues is further immobilised thereon.

According to another preferred embodiment of the present invention a) a peptide consisting of the amino acid sequence WRSELYKYKVVEIKPLGIAPTKAKRRVVEREKR (SEQ ID No. 5), or b) a homolog having at least 70% identity with a peptide of a), or c) a fragment of a peptide of a) or b) consisting of 15 to 32 amino acid residues is further immobilised thereon.

The solid support of the present invention may comprise more than one peptide, homolog or fragment as defined above immobilised thereon. Preferred combinations of such molecules include the following peptides and its respective homologs and fragments as defined above: SEQ ID No. 1 with SEQ ID No. 2; SEQ ID No. 1 with SEQ ID No. 3; SEQ ID No. 1 with SEQ ID No. 4; SEQ ID No. 1 with SEQ ID No. 5; SEQ ID No. 2 with SEQ ID No. 3; SEQ ID No. 2 with SEQ ID No. 4; SEQ ID No. 2 with SEQ ID No. 5; SEQ ID No. 1 with SEQ ID No. 2 and SEQ ID No. 3; SEQ ID No. 1 with SEQ ID No. 2 and SEQ ID No. 4; SEQ ID No. 1 with SEQ ID No. 2 and SEQ ID No. 5; SEQ ID No. 2 with SEQ ID No. 3 and SEQ ID No. 4; SEQ ID No. 2 with SEQ ID No. 3 and SEQ ID No. 5; SEQ ID No. 1 with SEQ ID No. 2, SEQ ID No. 3 and SEQ ID No. 4; SEQ ID No. 1 with SEQ ID No. 2, SEQ ID No. 3 and SEQ ID No. 5; SEQ ID No. 2 with SEQ ID No. 3, SEQ ID No. 4 and SEQ ID No. 5; SEQ ID No. 1 with SEQ ID No. 2, SEQ ID No. 3, SEQ ID No. 4 and SEQ ID No. 5. Of course it is also possible to combine this combinations with at least one, two, three, five, six, seven, eight, nine or ten of the peptides having SEQ ID No. 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41.

The solid support of the present invention may also comprise HIV-derived polypeptides. Therefore, according to a preferred embodiment of the present invention capsid protein p24 is further immobilised on said solid support.

According to another preferred embodiment of the present invention at least one polypeptide selected from the group consisting of HIV integrase, HIV reverse transcriptase+ RNAse H, HIV protease and HIV matrix protein p17 is further immobilised thereon.

The solid support is used to immobilise one or more of the peptides and/or polypeptides of the present invention. Depending on the further use of the solid support said solid support may have various forms. The solid support is preferably provided in the form of a column, bead, test tube, microtiter dish, solid particular, microchip or membrane. Such solid supports can be used in various immunoassays.

The present invention is further illustrated by the following figures and examples, however, without being restricted thereto.

FIG. 1 shows antibody responses to HIV-1 clade C gp120 and gp120-derived peptides. (A) Frequency (y-axes: number of reactive sera) of IgG, IgG subclass, IgA and IgM responses of African (left) and European (right) patients to recombinant gp120 and 24 overlapping gp120 peptides (x-axes: peptides 1-24). (B) Position of overlapping gp120 peptides in gp120 of the HIV-1 clade C South African strain (clade C_ZA) and of the reference strain HXB2 (clade B_HXB2). Gaps (numbers of missing amino acids are displayed) in gp120 from clade C and B required for optimal sequence alignment are indicated. Relevant protein domains described for gp120 clade B are indicated (SP: signal peptide, V1-V5: variable regions 1-5). (C) Multiple sequence alignment of the amino acid sequence of peptide 120/15 of HIV-1 clade C South African strain (Ref.C.ZA) with corresponding peptides from HIV-1 reference strains. Percentages of sequence identity with the Ref. C. ZA peptides are indicated on the right margin. Dots are conserved amino acids, dashes are gaps, N-linked glycosylation sites are underlined. The numbering system refers to HIV-1 strain HXB2 (Ref.B.FR) and "aa" stands for amino acid.

Figure 2A:
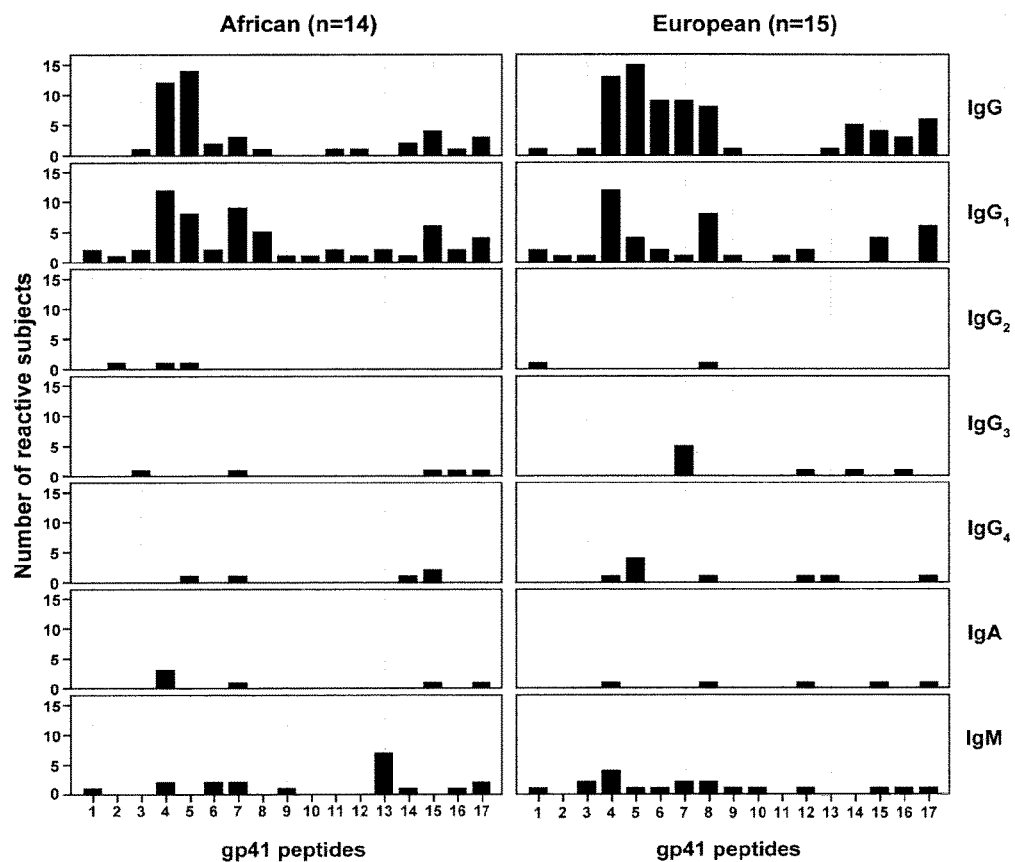
Figure 2B:
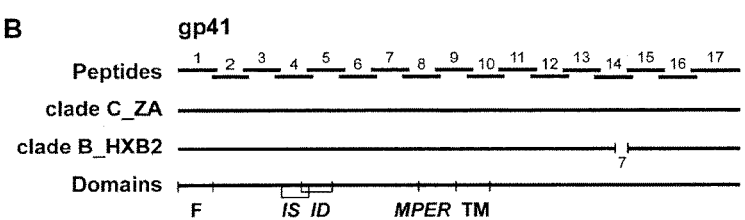

FIG. 2 shows antibody responses to HIV-1 clade C gp41-derived peptides. (A) Frequency (y-axes: number of reactive sera) of IgG, IgG subclass, IgA and IgM responses of African (left) and European (right) patients to 17 overlapping gp41 peptides (x-axes: peptides 1-17). (B) Position of overlapping gp41 peptides in gp41 of the HIV-1 clade C South African strain (clade C_ZA) and of the reference strain HXB2 (clade B_HXB2). A gap (number of missing amino acids is displayed) in gp41 from clade B required for optimal sequence alignment is indicated. Relevant protein domains/epitopes described for gp41 clade B are indicated (F: fusion peptide, TM: transmembrane domain, ID: immunodominant region, IS: immunosuppressive region, MPER: membrane proximal external region).

Figure 3A:
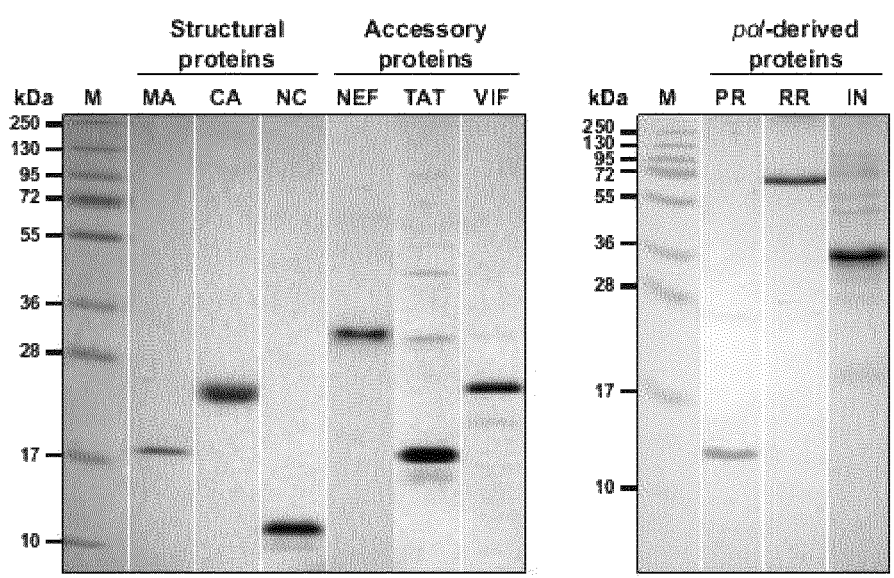

FIG. 3 shows purity and immunoreactivity of recombinant HIV1 clade C structural, accessory and pol-derived proteins. (A) Coomassie-stained SDS PAGE containing recombinant matrix (MA), capsid (CA), nucleocapsid (NC), NEF, TAT, VIF, protease (PR), reverse transcriptase+RNase H (RR), integrase (IN) and molecular weight markers (M). Molecular weights (kDa) are indicated on the left. (B) Frequency (y-axes: number of reactive sera) of IgG, IgG subclass, IgA and IgM responses of African (left) and European (right) patients to structural, accessory and pol-derived proteins (x-axes).

FIG. 4 shows IgG and IgM reactivity profiles to gp120-derived proteins and peptides of two individuals with negative results in established conventional HIV diagnostic tests. Shown are positive IgG and IgM antibody reactivities to HIV-1 clade C antigens (rgp120, MA: matrix; NEF, TAT, PR: protease, RR: reverse transcriptase+RNaseH, IN: integrase) and peptides. Negatine test results obtained with the InnoLIA IgG immunoblot for HIV-1 antigens gp120, gp41, integrase (IN), capsid (CA), matrix (MA) and HIV-2 antigens gp105, gp36 are shown on the right margin.

Figure 5C:
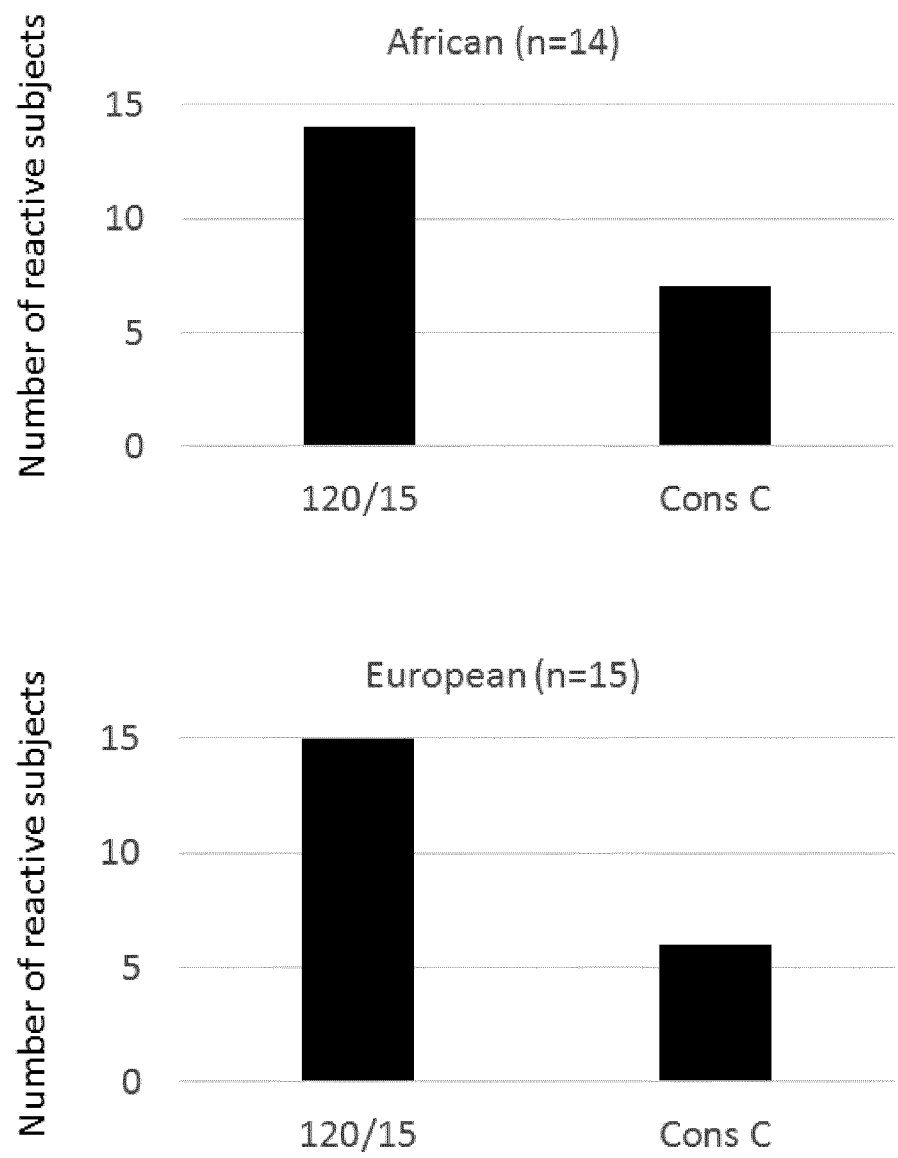

FIG. 5A shows an amino acid sequence alignment showing identical amino acids (*), substitutions (.) and gaps (-). The peptide length is indicated on the right margin as number of amino acids. The peptides aligned in FIG. 5A are AIVCTRPNNNTRKSIRIGPGQVFYT (SEQ ID No. 1) and NTRKSIRIGPGQTFY (SEQ ID No. 42; see Casseb et al. Braz J Med Biol Res 35(2002):369-375). FIG. 5B shows the medium IgG serum reactivity towards the two peptides of FIG. 5A in African and European HIV-infected patients, expressed as optical density (OD) subtracted of the reactivity to the negative control. Further the frequency (y-axes: number of reactive sera) of IgG responses of African (left) and European (right) patients to peptides having SEQ ID No. 1 and 42 is shown in FIG. 5C

EXAMPLES

Example 1

Materials and Methods

Synthesis of HIV-1 Clade C Envelope Overlapping Peptides

Twenty-four and 17 peptides covering the complete amino acid sequences of gp120 and gp41 from the South African HIV-1 clade C reference strain (isolate ZA.04.04ZASK146, Los Alamos HIV sequence database accession no. AY772699), were produced by solid phase synthesis on a CEM-Liberty (CEM, USA) or Applied Biosystems peptide synthesizer (Life technologies, USA). All peptides were 25 amino acids long, except the gp120 and gp41 C-terminal peptides accounting for 33 and 32 amino acids respectively, and had an overlap of 5 amino acids (see the following table).

HIV-1 Clade C Envelope Peptides:

| Peptides | Amino acid sequence | SEQ ID No. | Solvent |
|---|---|---|---|
| gp120 peptides | | | |
| 120/1 | RVRGILRNWPQWWIWGILGFWMIII | 6 | 10% DMF |
| 120/2 | WMIIICRGEENSWVTVYYGVPVWTE | 7 | 2% DMSO, 1 mM DTE |
| 120/3 | PVWTEAKTTLFCASDAKAYEKEVHN | 8 | PBS, 1 mM DTE |

-continued

| Peptides | Amino acid sequence | SEQ ID No. | Solvent |
|---|---|---|---|
| 120/4 | KEVHNVWATHACVPTDPSPQELVLE | 9 | H$_2$O, 1 mM DTE |
| 120/5 | ELVLENVTESFNMWENDMVDQMHED | 10 | H$_2$O, 9 mM NaOH |
| 120/6 | QMHEDIIGLWDESLKPCVKLTPLCV | 11 | H$_2$O, 1 mM DTE |
| 120/7 | TPLCVTLNCNTTSHNNSSPSPMTNC | 12 | 5% ACN, 1 mM DTE |
| 120/8 | PMTNCSFNATTELRDKTQKVNALFY | 13 | H$_2$O, 1 mM DTE |
| 120/9 | NALFYRSDIVPLEKNSSEYILINCN | 3 | 2% DMSO, 3 mM NaOH, 1 mM DTE |
| 120/10 | LINCNTSTITQACPKVSFDPIPIHY | 14 | 5% DMSO, 1 mM DTE |
| 120/11 | IPIHYCAPAGYAILKCNNKTFNGTG | 15 | H$_2$O, 1 mM DTE |
| 120/12 | FNGTGPCSNVSTVQCTHGIKPVVST | 16 | H$_2$O, 1 mM DTE |
| 120/13 | PVVSTQLLLNGSLAEGEIIRSENL | 17 | 3 mM NaOH |
| 120/14 | RSENLTDNAKTIIVHLNKSVAIVCT | 18 | H$_2$O, 1 mM DTE |
| 120/15 | AIVCTRPNNNTRKSIRIGPGQVFYT | 1 | H$_2$O, 1 mM DTE |
| 120/16 | QVFYTNEIIGNIRQAHCNISRELWN | 19 | 5% DMF, 1 mM DTE |
| 120/17 | RELWNNTLEQVKKKLKEHFQNKTIE | 20 | H$_2$O |
| 120/18 | NKTIEFQPPAGGDLEVTTHSFNCRG | 21 | H$_2$O, 1 mM DTE |
| 120/19 | FNCRGEFFYCNTSNLFNITASNASD | 22 | PBS, 2 mM NaOH, 1 mM DTE |
| 120/20 | SNASDANNNTITLPCKIKQIINMWQ | 23 | H$_2$O |
| 120/21 | INMWQEVGRAMYAPPIAGNITCNSS | 24 | 10% ACN, 1 mMDTE |
| 120/22 | TCNSSITGLLLTRDGGNNNDTGNNN | 25 | H$_2$O, 1 mM DTE |
| 120/23 | TGNNNDTEIFRPGGGNMKDNWRSEL | 26 | H$_2$O |
| 120/24 | WRSELYKYKVVEIKPLGIAPTKAKRRVVEREKR | 5 | H$_2$O |
| gp41 peptides | | | |
| 41/1 | AVGLGAVLLGFLGTAGSTMGAASIT | 27 | 5% ACN |
| 41/2 | AASITLTVQARQLLSGIVQQQSNLL | 28 | 5% DMF, 1 mM Acetic acid |
| 41/3 | QSNLLRAIEAQQHMLQLTVWGIKQL | 29 | H$_2$O |
| 41/4 | GIKQLQARVLAIERYLKDQQLLGLW | 4 | H$_2$O |
| 41/5 | LLGLWGCSGKLICTTAVHWNSSWSN | 2 | 5% DMSO, 1 mM DTE |
| 41/6 | SSWSNKSQDYIWGNMTWMQWDREIN | 30 | H$_2$O, 3 mM NaOH |
| 41/7 | DREINNYTDIIYTLLEESQSQQEKN | 31 | H$_2$O, 6 mM NaOH |
| 41/8 | QQEKNEKDLLALDSWNNLWNWFSIT | 32 | H$_2$O, 3 mM NaOH |
| 41/9 | WFSITKWLWYIKIFIMIVGGLIGLR | 33 | 2% DMSO |
| 41/10 | LIGLRIILGVLSIVKRVRQGYSPLS | 34 | 10% ACN |
| 41/11 | YSPLSFQTLPPNPRGPDRLRGIEEE | 35 | H$_2$O |
| 41/12 | GIEEEGGEQDKDRSIRLVSGFLALV | 36 | H$_2$O |
| 41/13 | FLALVWEDLRSLCLFSYHRLRDFIL | 37 | 5% DMF |
| 41/14 | RDFILIAGRAAELLGRSSLRGLQTG | 38 | H2O |
| 41/15 | GLQTGWQALKYLGSLVQYWGLELKK | 39 | 5% ACN |
| 41/16 | LELKKSAINLFDTTAIVVAEGTDRL | 40 | 2% DMSO, 2 mM NaOH |
| 41/17 | GTDRLIEGLQGIGRAIYNIPRRIRQGFEAALL | 41 | 2% DMF |

The synthesis was performed with the 9-fluorenyl-methoxycarbonyl (Fmoc)-method, using PEG-PS preloaded resins. Synthesized peptides were washed with dichloromethane, cleaved from the resins in a mixture of 19 ml trifluoroacetic acid, 500 ul silane and 500 ul H$_2$O and precipitated into tert-butylmethylether. Peptides were separated from by-products by reverse-phase HPLC in an acetonitrile gradient (UltiMate 3000 Pump, Dionex, USA) to a purity >90% and their identity was verified by mass spectrometry (Microflex MALDI-TOF, Bruker, USA). The peptides' chemical features were predicted by ProtParam on the Expasy proteomics server and were considered in the optimization of the solubilisation conditions. Highly hydrophobic peptides were solubilised in dimethylformamide (DMF), dimethylsulfoxide (DMSO) or acetonitrile (ACN), while reducing agents such as dithioerythritol (DTE) were added to peptides rich in Cysteins and NaOH to strongly acidic peptides.

Expression and Purification of Recombinant HIV-1 Clade C Proteins

Recombinant matrix (MA), capsid (CA), nucleocapsid (NC) proteins as well as accessory NEF, TAT and VIF and the pol-derived protease (PR), reverse transcriptase+RNAseH (RR) and integrase (IN) were expressed in *Escherichia coli* (*E. coli*). Briefly, the cDNA sequences of the structural and accessory proteins as well as of the protease were derived from the HIV-1 clade C reference strain from South Africa (isolate ZA.04.04ZASK146, Los Alamos HIV sequence database accession no. AY772699). The reverse transcriptase-RNAseH and the integrase constructs were derived from the Ethiopian HIV-1 clade C isolate ET.86.ETH2220 (Los Alamos HIV sequence database accession no. U46016). The cDNA of the proteins, followed by a hexa-histidine tag, was codon-optimized for bacterial expression and cloned into a pET17b vector (ATG: biosynthetics, Germany). Expression of the recombinant proteins in *E. coli* BL21(DE3) cells, grown to an OD$_{600}$=0.4-0.6 in LB medium supplemented with 100 mg/l ampicillin, was induced by addition of 0.5-1.0 mM isopropyl-β-thiogalactopyranoside (IPTG) and proteins were purified by Nickel-affinity chromatography under native or denaturing conditions. For purification under native conditions of matrix, capsid and nucleocapsid proteins, cells were lysed in 50 mM NaH$_2$PO$_4$, 300 mM NaCl, 10 mM Imidazole pH8.0, PMSF (1 μl/ml), Lysozyme (1 mg/ml) by sequential cycles of freezing and thawing; DNA was cleaved by treatment with 5 μg/ml DNaseI (20 min at room temperature); and, after removal of cellular debris (by centrifugation at 18000 rpm, 20 min, 4° C.), the clear lysate was incubated with Nickel-agarose (QIAGEN, Germany) 2-4 h at 4° C.

Elution of the His-tagged proteins was performed with an imidazole gradient (20, 50, 100, 250 mM Imidazole) in 50 mM NaH$_2$PO$_4$, 300 mM NaCl pH 8.0. For purification of NEF, TAT and protease under denaturing conditions, cells were lysed in 8M Urea or 6M Guanidinium chloride buffer for at least 2 h or overnight at room temperature. After removal of cellular debris (by centrifugation at 18000 rpm, 20 min, 4° C.) and incubation of the clear lysate with Nickel-agarose (QIAGEN, Germany) (2-4 h at room temperature or overnight at 4° C.), a pH gradient (pH 6.3, 5.6, 4.5) was used to elute the recombinant proteins in 8M Urea, 100 mM NaH$_2$PO$_4$, 10 mM Tris. For purification of recombinant integrase, the cells were first lysed under native conditions as described above, and, since after centrifugation (18000 rpm, 20 min, 4° C.) the protein was found in the insoluble fraction, this was resuspended in 8M Urea, 100 mM NaH$_2$PO$_4$, 10 mM Tris, pH8.0 and incubated at room temperature overnight. After removal of cellular debris (by a second step of centrifugation at 18000 rpm, 20 min, 4° C.), the recombinant integrase was purified under denaturing conditions in 8M Urea as described above. Purification of VIF and reverse transcriptase+RNAseH was achieved by using an inclusion body preparation protocol. Removal of urea and refolding of the recombinant proteins purified under denaturing conditions were achieved by sequential dialysis steps.

The identity of the proteins was verified by SDS-PAGE and Coomassie staining (FIG. 3A) as well as by Westernblot and by mass spectrometry. Their secondary structure and thermal stability were analyzed by Circular dichroism spectroscopy on a Jasko J-810 spectropolarimeter (Japan Spectroscopic, Japan). The biochemical features of the recombinant HIV-1 clade C proteins, predicted with the ProtParam software on the Expasy server and assessed experimentally as described above, are outlined in the following table.

Biochemical features of recombinant HIV-1 clade C proteins:

| Proteins[1] | MW[2] kDa | Migration SDS-PAGE kDa | pI[4] | Secondary structure[4] | Thermal Stability[5] |
|---|---|---|---|---|---|
| MA | 15.5 | 17.5 | 9.1 | α-helical > β-sheet | Tm = 65° C. |
| CA | 26.5 | 24.0 | 6.6 | α-helical | Tm = 66° C. |
| NC | 7.2 | 11.0 | 10.2 | β-sheet < random coil | n.d. |
| NEF | 24.6 | 30.0 | 6.2 | α-helical & β-sheet | n.d. |
| TAT | 12.2 | 17.0 | 9.0 | Random coil | n.d. |
| VIF | 23.7 | 24.0 | 10.5 | β-sheet > α-helical | Tm > 95° C. |
| PR | 11.7 | 12.0 | 8.7 | β-sheet & random coil | Tm = 55° C. |
| RR | 65.1 | 65.0 | 6.8 | α-helical & β-sheet | Tm > 95° C. |
| IN | 33.2 | 33.5 | 7.4 | α-helical & β-sheet | n.d. |

[1]Protein abbreviations: MA: matrix, CA: capsid, NC: nucleocapsid, PR: protease, RR: reverse transcriptase + RNAseH, IN: integrase.
[2]MW: Molecular weight in kilo Daltons (kDa), as predicted with ProtParam and verified by mass spectrometry.
[3]pI: Isoelectrical point predicted with ProtParam.
[4]Secondary structure: determined by circular dichroism spectroscopy, predominance of alpha-helical or beta-sheet elements.
[5]Thermal stability: determined by circular dichroism spectroscopy;
Tm: melting temperature; n.d.: not done.

Study Subjects and Routine Immunoassays

Sera were taken from 14 African HIV-infected patients, from 2 highly exposed African individuals, from 15 European HIV-infected patients and from 10 uninfected individuals. HIV seropositivity and -negativity was confirmed for each of the subjects by routine analyses. HIV-specific IgG immunoblots were carried out by Line Immuno Assay (InnoLIA, Innogenetics, Belgium) and asymptomatic subjects were additionally tested with the Abbott Murex HIV Ag/Ab combination (Abbott, USA).

HIV-1 Clade C Specific IgG, IgA and IgM Determinations by ELISA

ELISA plates (Nunc Maxisorp, Thermo Fisher Scientific, USA) were coated overnight at 4° C. with the HIV-1 clade C derived peptides and proteins diluted in 100 mM sodium bicarbonate buffer pH 9.6 (2 ug/ml). After washing in PBS, 0.05% v/v Tween20 and blocking in 2% w/v BSA, PBS, 0.05% v/v Tween20 for at least 4 h at room temperature, the plates were incubated with sera diluted 1:200 in 0.5% w/v BSA, PBS, 0.05% v/v Tween20 overnight at 4° C. Bound antibodies were detected with mouse anti-human IgG$_1$, IgG$_2$, IgG$_4$, IgA, IgM (BD, 1:1000, 2 h at room temperature) or mouse anti-human IgG$_3$ (1:5000, 2 h at room temperature, Sigma Aldrich, St. Louis, Mo.) and horseradish peroxidase (HRP)-coupled sheep anti-mouse IgG (1:2000, 1 h at room temperature, GE Healthcare, Waukesha, Wis.). Total IgG antibodies were detected with a directly labelled HRP-anti human IgG (1:5000, 1 h at room temperature, GE Healthcare, USA). The colour reaction was induced with 2,2'-azino-bis(3-ethylbenzothiazoline-6-sulfonic acid)di-ammonium salt and the optical density (OD$_{405nm}$-OD$_{490nm}$) was measured on a Spectra Max spectrophotometer (Molecular Devices, USA). As control antigen for the analysis of envelope-specific reactivity, we used recombinant His-tagged gp120 from HIV-1 clade C, isolate CN54, expressed in 293 cells (#11233-V08H, Sino Biological, China). For inter-plate normalization we analysed on each plate a positive control serum specific for each antibody isotype/subclass. Additionally, reactivity of each serum sample to human serum albumin (HSA) was tested as negative control. Coating of the antigens was verified by detection of His-tagged proteins with a mouse anti-His-tag antibody (Dianova, Germany) and by detection of untagged proteins and peptides with a pool of HIV-infected sera. Unspecific binding of the detection antibodies to coated antigens was excluded by buffer control analyses. All determinations were carried out as duplicates and results are shown as normalized means of the raw data subtracted by the reactivity to the negative control antigen. Cut-off values were calculated for each antibody isotype/subclass and for each antigen as the mean+3SD of the results of the HIV uninfected subjects.

For multiple sequence alignments, the amino acid sequence identity was calculated with ClustalW2 on the EMBL-EBI server and alignments were generated with the programme Gene Doc. Sequences are numbered accordingly to the international HXB2 numbering scheme, with amino acid insertions carrying the number of the last corresponding HXB2 amino acid followed by sequential letters.

Results

Almost Identical IgG, IgA and IgM Responses Towards Gp120 Epitopes from HIV-1 Clade C in HIV-Infected Patients from Africa and Europe For a detailed epitope mapping of gp120, sera from HIV-1-infected patients from Zimbabwe were tested, where clade C is the predominant HIV-1 subtype, and from European patients infected with HIV-1 strains from different clades for antibody reactivity with recombinant gp120 and 24 gp120-derived overlapping peptides. These peptides covered the complete amino acid sequence of gp120 derived from the South African HIV-1 subtype C reference strain (FIG. 1 A, B). IgG, IgA, IgM and IgG$_{1-4}$ subclass reactivities were measured.

Figure 1B:
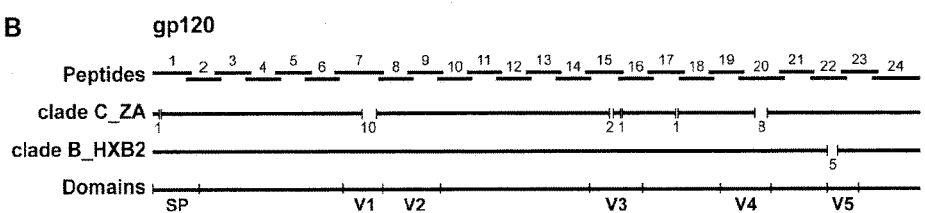

Interestingly, IgG, IgG subclass, IgA and IgM response profiles towards the peptides were almost identical in the African (FIG. 1A, left panel) and in the European (FIG. 1A, right panel) HIV-infected patients. The recognition pattern of the peptides was similar for all antibody classes and the IgG subclasses. However, the analysis of antibody levels and frequencies of recognition showed that IgG and in particular IgG$_1$ responses dominated in both populations. Peptide 120/15 was the major antibody-reactive peptide in terms of frequency and intensity of recognition for the African and European patients (FIG. 1A). Peptide 120/24 was also recognized by a majority of the individuals tested. The overview of gp120 (FIG. 1B) shows that peptide 120/15 resides in the V3 domain, which is supposed to contain a binding site for the co-receptor CCR5/CXCR4 on CD4 cells. Peptide 120/24 is located at the very C-terminal end of gp120.

FIG. 1C contains a sequence alignment of peptide 120/15 with the corresponding peptides in various HIV-1 reference strains from different continents. A considerable degree of sequence variation of the peptide 120/15-corresponding regions was found among the strains, ranging from 88 to 72% sequence identity. Depending on the strain, the peptide 120/15-defined region contains one or two N-linked glycosylation sites.

African and European Patients Recognize Highly Similar Epitopes on Gp41 from HIV-1 Clade C Next, the IgG, IgA and IgM responses of the African and European patients to 17 overlapping peptides derived from HIV-1 clade C gp41 was analysed (FIGS. 2A, B). Again it was found that the African and European patients recognized similar peptides and that the immune response was dominated by IgG and in particular by IgG$_1$ antibodies. Both the frequency and the intensity of recognition were lower towards the gp41 peptides than to the gp120-derived peptides. IgG and IgG$_1$ antibodies were directed mainly to a region defined by peptides 41/4-8 (FIG. 2A). This region includes areas, which have been designated as "immunosuppressive" and "immunodominant" domains and contain the majority of the predicted N-linked glycosylation sites of gp41 (FIGS. 2A, B). Interestingly, the other antibody-reactive area defined by peptides 41/14-17 was located at the C-terminal portion of gp41, which is part of the so-called "cytoplasmic domain".

Figure 3B:
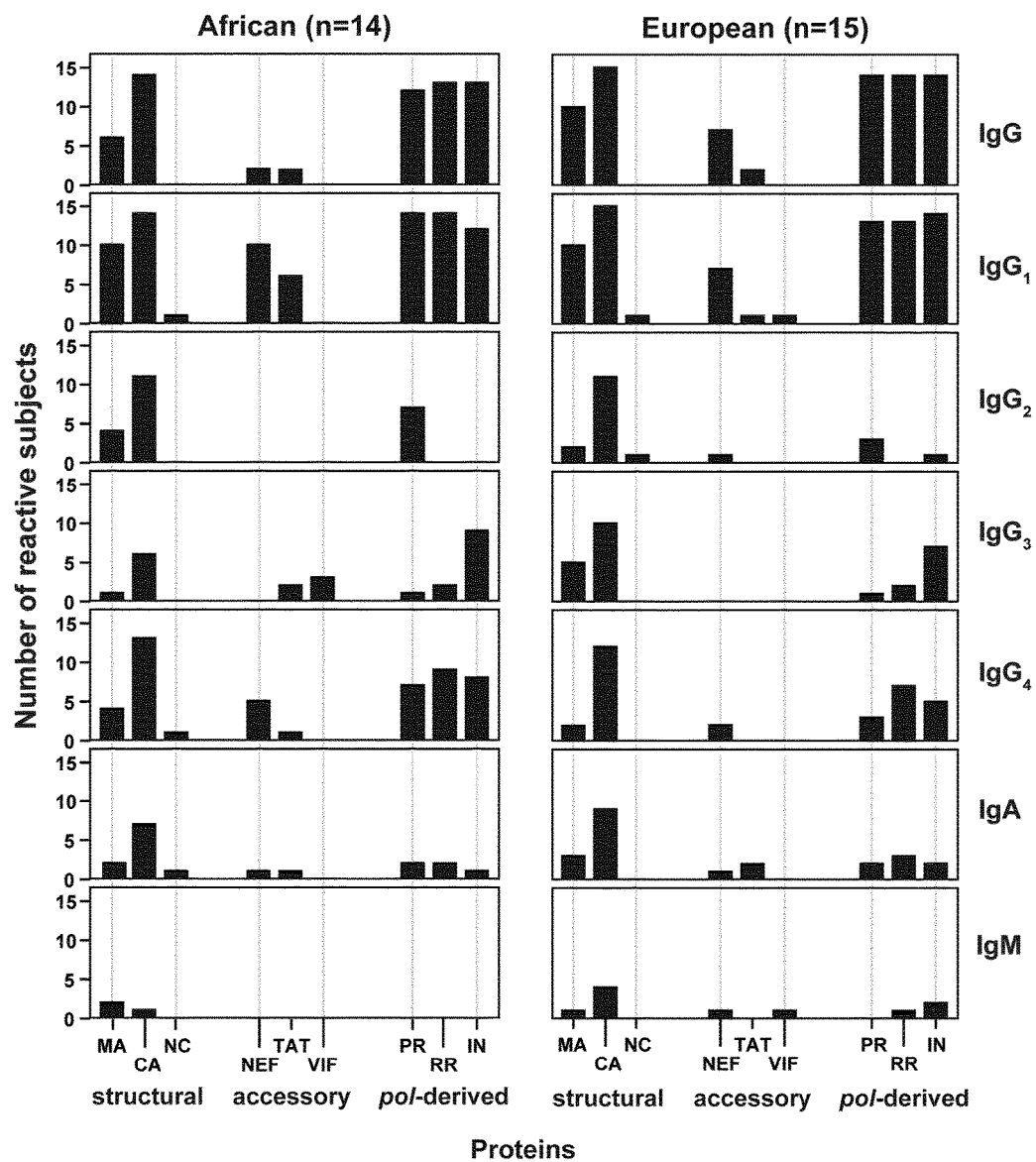

African and European HIV-Infected Patients React Primarily with Structural and Pol-Derived but not with Accessory Proteins In order to characterize the antibody response directed to viral proteins other than the surface antigens, HIV-1 clade C structural, pol-derived and accessory proteins were expressed in *E. coli* and purified and the protein-specific antibody levels were measured in African (FIG. 3B, left panel) and European sera (FIG. 3B, right panel). Similar as for the envelope proteins, the immune response was dominated by IgG and in particular by IgG$_1$ antibodies. Again patients of both populations showed a similar recognition profile: The protease, reverse transcriptase+RNAseH, integrase, as well as the capsid protein and the matrix protein were the most frequently and strongly recognized antigens. Antibody responses towards the nucleocapsid protein and the accessory proteins were rare and low.

IgG Subclass Recognition of HIV Proteins and Peptides is Indicative of Mixed Th1/Th2 Immune Response The measurements of IgG subclass responses towards the gp120 and gp41 peptides as well as against the structural, pol-derived and accessory proteins were performed using the same serum dilution. Since IgG$_1$ represents the dominating IgG subclass, IgG$_1$ responses were more intense and frequent than IgG$_2$, IgG$_3$ and IgG$_4$ responses. However, the antigen and epitope recognition profile was similar for all subclasses in the African and European patients. The frequencies and intensities of IgG$_2$ and IgG$_4$ responses were comparable, which is indicative of a mixed Th1/Th2 immune response.

High Sensitivity and Specificity of Diagnostic Tests Based on Recombinant Proteins and Peptides Assembling the Clade C Proteome The comprehensive analysis of antibody responses showed that the panel of HIV-1 clade C-derived antigens and peptides allowed the reliable detection of specific IgG antibodies in each of the HIV-infected patients from Africa and Europe. No false positive test results were obtained when sera from uninfected individuals were tested. Peptide 120/15 was as good as complete rgp120 for IgG-based diagnosis of HIV-infected patients because it allowed identifying 29 out of the 29 patients. Likewise, peptide 41/5 allowed identifying 29 out of 29 patients whereas peptide 120/24 was positive in 21 patients. Testing for IgG reactivity to the capsid protein identified 29/29, to reverse transcriptase+RNAseH 27/29, to integrase 27/29 and to protease 26/29 patients. Peptides 120/15 and 41/5 can therefore be used alone to diagnose HIV infections in individuals. Using a panel of peptides 120/15, 120/24, rgp120, capsid and pol-derived proteins each of the infected patients was diagnosed by IgG testing.

Furthermore, it was found that HIV-highly exposed African individuals with an infection, who were negative in routine antigen/IgG+IgM determinations (Abbott Murex HIV Ag/Ab combination, Abbott, USA) as well as in Immunoblot-based assays (InnoLIA, Innogenetics, Belgium; shown in FIG. 4, right margin), could be diagnosed by IgG and IgM testing to the panel of HIV-1 clade C-derived antigens and peptides (FIG. 4).

Example 2

In this example the reactivity of the peptides having the amino acid sequence AIVCTRPNNNTRKSIRIGPGQVFYT (SEQ ID No. 1; "120/15") and NTRKSIRIGPGQTFY (SEQ ID No. 42; "Cons C", see Casseb et al. Braz J Med Biol Res 35(2002):369-375) with serum of HIV infected individuals is examined. The results of this example are depicted in FIG. 5.

FIG. 5A shows a comparison of the amino acid sequences of peptide 120/15 and the consensus peptide Cons C used by Casseb et al. 2002, which has been made to incorporate a Threonine in position 13 to resemble the sequences of most of the subtype C sequences, whereas 120/15 contains a Valine in this position. Despite the fact that the sequence of the consensus peptide was modified to resemble the amino acid sequence of most of the subtype C sequences, 11 out of 29 HIV-positive serum samples did not react with this peptide and hence were false negative in the diagnostic test, whereas peptide 120/15 allowed to identify each of the 29 HIV-positive serum samples (see FIG. 5C).

Materials and Methods

The peptide "Cons C" which was used by Casseb et al. 2002, was manufactured using solid phase peptide synthesis, as described for the gp120-derived peptides (see example 1). For ELISA experiments the peptides were solubilized in H$_2$O, and the immunological assays were performed as described for the gp120-derived peptides (see example 1).

The invention claimed is:

1. A solid support comprising
   a peptide consisting of the amino acid sequence selected from the group consisting of SEQ ID NOs. 1-5.

2. The solid support according to claim 1, wherein
   a) the peptide consisting of the amino acid sequence SEQ ID No. 2.

3. The solid support according to claim 1, wherein
   a) the peptide consisting of the amino acid sequence SEQ ID No. 3.

4. The solid support according to claim 1, wherein
   a) the peptide consisting of the amino acid sequence SEQ ID No. 4.

5. The solid support according to claim 1, wherein
   a) the peptide consisting of the amino acid sequence SEQ ID No. 5.

6. The solid support according to claim 1, wherein capsid protein p24 is immobilized thereon.

7. The solid support according to claim 1, wherein at least one polypeptide selected from the group consisting of HIV integrase, HIV reverse transcriptase+RNAse H, HIV protease and HIV matrix protein p17 is immobilized thereon.

8. The solid support according to claim 1, wherein the solid support is selected from the group consisting of a column, bead, test tube, microtiter dish, solid particular, microchip and membrane.

9. The solid support according to claim 1, wherein
   a) the peptide consisting of the amino acid sequence SEQ ID NO. 1.

* * * * *

SEQUENCE LISTING

<160> NUMBER OF SEQ ID NOS: 71

<210> SEQ ID NO 1
<211> LENGTH: 25
<212> TYPE: PRT
<213> ORGANISM: Artificial Sequence
<220> FEATURE:
<223> OTHER INFORMATION: Peptide

<400> SEQUENCE: 1

Ala Ile Val Cys Thr Arg Pro Asn Asn Thr Arg Lys Ser Ile Arg
1               5                   10                  15

Ile Gly Pro Gly Gln Val Phe Tyr Thr
            20                  25

<210> SEQ ID NO 2
<211> LENGTH: 25
<212> TYPE: PRT
<213> ORGANISM: Artificial Sequence
<220> FEATURE:
<223> OTHER INFORMATION: Peptide

<400> SEQUENCE: 2

Leu Leu Gly Leu Trp Gly Cys Ser Gly Lys Leu Ile Cys Thr Thr Ala
1               5                   10                  15

Val His Trp Asn Ser Ser Trp Ser Asn
            20                  25

<210> SEQ ID NO 3
<211> LENGTH: 25
<212> TYPE: PRT
<213> ORGANISM: Artificial Sequence
<220> FEATURE:
<223> OTHER INFORMATION: Peptide

<400> SEQUENCE: 3

Asn Ala Leu Phe Tyr Arg Ser Asp Ile Val Pro Leu Glu Lys Asn Ser
1               5                   10                  15

Ser Glu Tyr Ile Leu Ile Asn Cys Asn
            20                  25

<210> SEQ ID NO 4
<211> LENGTH: 25
<212> TYPE: PRT
<213> ORGANISM: Artificial Sequence
<220> FEATURE:
<223> OTHER INFORMATION: Peptide

<400> SEQUENCE: 4

Gly Ile Lys Gln Leu Gln Ala Arg Val Leu Ala Ile Glu Arg Tyr Leu
1               5                   10                  15

Lys Asp Gln Gln Leu Leu Gly Leu Trp
            20                  25

<210> SEQ ID NO 5
<211> LENGTH: 33
<212> TYPE: PRT
<213> ORGANISM: Artificial Sequence
<220> FEATURE:
<223> OTHER INFORMATION: Peptide

<400> SEQUENCE: 5

Trp Arg Ser Glu Leu Tyr Lys Tyr Lys Val Val Glu Ile Lys Pro Leu
1               5                   10                  15

Gly Ile Ala Pro Thr Lys Ala Lys Arg Arg Val Val Glu Arg Glu Lys
                20                  25                  30

Arg

<210> SEQ ID NO 6
<211> LENGTH: 25
<212> TYPE: PRT
<213> ORGANISM: Artificial Sequence
<220> FEATURE:
<223> OTHER INFORMATION: Peptide

<400> SEQUENCE: 6

Arg Val Arg Gly Ile Leu Arg Asn Trp Pro Gln Trp Trp Ile Trp Gly
1               5                   10                  15

Ile Leu Gly Phe Trp Met Ile Ile Ile
                20                  25

<210> SEQ ID NO 7
<211> LENGTH: 25
<212> TYPE: PRT
<213> ORGANISM: Artificial Sequence
<220> FEATURE:
<223> OTHER INFORMATION: Peptide

<400> SEQUENCE: 7

Trp Met Ile Ile Ile Cys Arg Gly Glu Glu Asn Ser Trp Val Thr Val
1               5                   10                  15

Tyr Tyr Gly Val Pro Val Trp Thr Glu
                20                  25

<210> SEQ ID NO 8
<211> LENGTH: 25
<212> TYPE: PRT
<213> ORGANISM: Artificial Sequence
<220> FEATURE:
<223> OTHER INFORMATION: Peptide

<400> SEQUENCE: 8

Pro Val Trp Thr Glu Ala Lys Thr Thr Leu Phe Cys Ala Ser Asp Ala
1               5                   10                  15

Lys Ala Tyr Glu Lys Glu Val His Asn
                20                  25

<210> SEQ ID NO 9
<211> LENGTH: 25
<212> TYPE: PRT
<213> ORGANISM: Artificial Sequence
<220> FEATURE:
<223> OTHER INFORMATION: Peptide

<400> SEQUENCE: 9

Lys Glu Val His Asn Val Trp Ala Thr His Ala Cys Val Pro Thr Asp
1               5                   10                  15

Pro Ser Pro Gln Glu Leu Val Leu Glu
                20                  25

<210> SEQ ID NO 10
<211> LENGTH: 25
<212> TYPE: PRT
<213> ORGANISM: Artificial Sequence

```
<220> FEATURE:
<223> OTHER INFORMATION: Peptide

<400> SEQUENCE: 10

Glu Leu Val Leu Glu Asn Val Thr Glu Ser Phe Asn Met Trp Glu Asn
1               5                   10                  15

Asp Met Val Asp Gln Met His Glu Asp
            20                  25

<210> SEQ ID NO 11
<211> LENGTH: 25
<212> TYPE: PRT
<213> ORGANISM: Artificial Sequence
<220> FEATURE:
<223> OTHER INFORMATION: Peptide

<400> SEQUENCE: 11

Gln Met His Glu Asp Ile Ile Gly Leu Trp Asp Glu Ser Leu Lys Pro
1               5                   10                  15

Cys Val Lys Leu Thr Pro Leu Cys Val
            20                  25

<210> SEQ ID NO 12
<211> LENGTH: 25
<212> TYPE: PRT
<213> ORGANISM: Artificial Sequence
<220> FEATURE:
<223> OTHER INFORMATION: Peptide

<400> SEQUENCE: 12

Thr Pro Leu Cys Val Thr Leu Asn Cys Asn Thr Thr Ser His Asn Asn
1               5                   10                  15

Ser Ser Pro Ser Pro Met Thr Asn Cys
            20                  25

<210> SEQ ID NO 13
<211> LENGTH: 25
<212> TYPE: PRT
<213> ORGANISM: Artificial Sequence
<220> FEATURE:
<223> OTHER INFORMATION: Peptide

<400> SEQUENCE: 13

Pro Met Thr Asn Cys Ser Phe Asn Ala Thr Thr Glu Leu Arg Asp Lys
1               5                   10                  15

Thr Gln Lys Val Asn Ala Leu Phe Tyr
            20                  25

<210> SEQ ID NO 14
<211> LENGTH: 25
<212> TYPE: PRT
<213> ORGANISM: Artificial Sequence
<220> FEATURE:
<223> OTHER INFORMATION: Peptide

<400> SEQUENCE: 14

Leu Ile Asn Cys Asn Thr Ser Thr Ile Thr Gln Ala Cys Pro Lys Val
1               5                   10                  15

Ser Phe Asp Pro Ile Pro Ile His Tyr
            20                  25
```

```
<210> SEQ ID NO 15
<211> LENGTH: 25
<212> TYPE: PRT
<213> ORGANISM: Artificial Sequence
<220> FEATURE:
<223> OTHER INFORMATION: Peptide

<400> SEQUENCE: 15

Ile Pro Ile His Tyr Cys Ala Pro Ala Gly Tyr Ala Ile Leu Lys Cys
1               5                   10                  15

Asn Asn Lys Thr Phe Asn Gly Thr Gly
            20                  25

<210> SEQ ID NO 16
<211> LENGTH: 25
<212> TYPE: PRT
<213> ORGANISM: Artificial Sequence
<220> FEATURE:
<223> OTHER INFORMATION: Peptide

<400> SEQUENCE: 16

Phe Asn Gly Thr Gly Pro Cys Ser Asn Val Ser Thr Val Gln Cys Thr
1               5                   10                  15

His Gly Ile Lys Pro Val Val Ser Thr
            20                  25

<210> SEQ ID NO 17
<211> LENGTH: 25
<212> TYPE: PRT
<213> ORGANISM: Artificial Sequence
<220> FEATURE:
<223> OTHER INFORMATION: Peptide

<400> SEQUENCE: 17

Pro Val Val Ser Thr Gln Leu Leu Leu Asn Gly Ser Leu Ala Glu Gly
1               5                   10                  15

Glu Ile Ile Ile Arg Ser Glu Asn Leu
            20                  25

<210> SEQ ID NO 18
<211> LENGTH: 25
<212> TYPE: PRT
<213> ORGANISM: Artificial Sequence
<220> FEATURE:
<223> OTHER INFORMATION: Peptide

<400> SEQUENCE: 18

Arg Ser Glu Asn Leu Thr Asp Asn Ala Lys Thr Ile Ile Val His Leu
1               5                   10                  15

Asn Lys Ser Val Ala Ile Val Cys Thr
            20                  25

<210> SEQ ID NO 19
<211> LENGTH: 25
<212> TYPE: PRT
<213> ORGANISM: Artificial Sequence
<220> FEATURE:
<223> OTHER INFORMATION: Peptide

<400> SEQUENCE: 19

Gln Val Phe Tyr Thr Asn Glu Ile Ile Gly Asn Ile Arg Gln Ala His
1               5                   10                  15

Cys Asn Ile Ser Arg Glu Leu Trp Asn
            20                  25
```

```
<210> SEQ ID NO 20
<211> LENGTH: 25
<212> TYPE: PRT
<213> ORGANISM: Artificial Sequence
<220> FEATURE:
<223> OTHER INFORMATION: Peptide

<400> SEQUENCE: 20

Arg Glu Leu Trp Asn Thr Leu Glu Gln Val Lys Lys Leu Lys
1               5                   10                  15

Glu His Phe Gln Asn Lys Thr Ile Glu
            20                  25

<210> SEQ ID NO 21
<211> LENGTH: 25
<212> TYPE: PRT
<213> ORGANISM: Artificial Sequence
<220> FEATURE:
<223> OTHER INFORMATION: Peptide

<400> SEQUENCE: 21

Asn Lys Thr Ile Glu Phe Gln Pro Pro Ala Gly Gly Asp Leu Glu Val
1               5                   10                  15

Thr Thr His Ser Phe Asn Cys Arg Gly
            20                  25

<210> SEQ ID NO 22
<211> LENGTH: 25
<212> TYPE: PRT
<213> ORGANISM: Artificial Sequence
<220> FEATURE:
<223> OTHER INFORMATION: Peptide

<400> SEQUENCE: 22

Phe Asn Cys Arg Gly Glu Phe Phe Tyr Cys Asn Thr Ser Asn Leu Phe
1               5                   10                  15

Asn Ile Thr Ala Ser Asn Ala Ser Asp
            20                  25

<210> SEQ ID NO 23
<211> LENGTH: 25
<212> TYPE: PRT
<213> ORGANISM: Artificial Sequence
<220> FEATURE:
<223> OTHER INFORMATION: Peptide

<400> SEQUENCE: 23

Ser Asn Ala Ser Asp Ala Asn Asn Thr Ile Thr Leu Pro Cys Lys
1               5                   10                  15

Ile Lys Gln Ile Ile Asn Met Trp Gln
            20                  25

<210> SEQ ID NO 24
<211> LENGTH: 25
<212> TYPE: PRT
<213> ORGANISM: Artificial Sequence
<220> FEATURE:
<223> OTHER INFORMATION: Peptide

<400> SEQUENCE: 24

Ile Asn Met Trp Gln Glu Val Gly Arg Ala Met Tyr Ala Pro Pro Ile
1               5                   10                  15

Ala Gly Asn Ile Thr Cys Asn Ser Ser
            20                  25
```

```
<210> SEQ ID NO 25
<211> LENGTH: 25
<212> TYPE: PRT
<213> ORGANISM: Artificial Sequence
<220> FEATURE:
<223> OTHER INFORMATION: Peptide

<400> SEQUENCE: 25

Thr Cys Asn Ser Ser Ile Thr Gly Leu Leu Thr Arg Asp Gly Gly
1               5                   10                  15

Asn Asn Asn Asp Thr Gly Asn Asn Asn
            20                  25

<210> SEQ ID NO 26
<211> LENGTH: 25
<212> TYPE: PRT
<213> ORGANISM: Artificial Sequence
<220> FEATURE:
<223> OTHER INFORMATION: Peptide

<400> SEQUENCE: 26

Thr Gly Asn Asn Asn Asp Thr Glu Ile Phe Arg Pro Gly Gly Asn
1               5                   10                  15

Met Lys Asp Asn Trp Arg Ser Glu Leu
            20                  25

<210> SEQ ID NO 27
<211> LENGTH: 25
<212> TYPE: PRT
<213> ORGANISM: Artificial Sequence
<220> FEATURE:
<223> OTHER INFORMATION: Peptide

<400> SEQUENCE: 27

Ala Val Gly Leu Gly Ala Val Leu Leu Gly Phe Leu Gly Thr Ala Gly
1               5                   10                  15

Ser Thr Met Gly Ala Ala Ser Ile Thr
            20                  25

<210> SEQ ID NO 28
<211> LENGTH: 25
<212> TYPE: PRT
<213> ORGANISM: Artificial Sequence
<220> FEATURE:
<223> OTHER INFORMATION: Peptide

<400> SEQUENCE: 28

Ala Ala Ser Ile Thr Leu Thr Val Gln Ala Arg Gln Leu Leu Ser Gly
1               5                   10                  15

Ile Val Gln Gln Gln Ser Asn Leu Leu
            20                  25

<210> SEQ ID NO 29
<211> LENGTH: 25
<212> TYPE: PRT
<213> ORGANISM: Artificial Sequence
<220> FEATURE:
<223> OTHER INFORMATION: Peptide

<400> SEQUENCE: 29

Gln Ser Asn Leu Leu Arg Ala Ile Glu Ala Gln Gln His Met Leu Gln
1               5                   10                  15

Leu Thr Val Trp Gly Ile Lys Gln Leu
            20                  25
```

```
<210> SEQ ID NO 30
<211> LENGTH: 25
<212> TYPE: PRT
<213> ORGANISM: Artificial Sequence
<220> FEATURE:
<223> OTHER INFORMATION: Peptide

<400> SEQUENCE: 30

Ser Ser Trp Ser Asn Lys Ser Gln Asp Tyr Ile Trp Gly Asn Met Thr
1               5                   10                  15

Trp Met Gln Trp Asp Arg Glu Ile Asn
            20                  25

<210> SEQ ID NO 31
<211> LENGTH: 25
<212> TYPE: PRT
<213> ORGANISM: Artificial Sequence
<220> FEATURE:
<223> OTHER INFORMATION: Peptide

<400> SEQUENCE: 31

Asp Arg Glu Ile Asn Asn Tyr Thr Asp Ile Ile Tyr Thr Leu Leu Glu
1               5                   10                  15

Glu Ser Gln Ser Gln Gln Glu Lys Asn
            20                  25

<210> SEQ ID NO 32
<211> LENGTH: 25
<212> TYPE: PRT
<213> ORGANISM: Artificial Sequence
<220> FEATURE:
<223> OTHER INFORMATION: Peptide

<400> SEQUENCE: 32

Gln Gln Glu Lys Asn Glu Lys Asp Leu Leu Ala Leu Asp Ser Trp Asn
1               5                   10                  15

Asn Leu Trp Asn Trp Phe Ser Ile Thr
            20                  25

<210> SEQ ID NO 33
<211> LENGTH: 25
<212> TYPE: PRT
<213> ORGANISM: Artificial Sequence
<220> FEATURE:
<223> OTHER INFORMATION: Peptide

<400> SEQUENCE: 33

Trp Phe Ser Ile Thr Lys Trp Leu Trp Tyr Ile Lys Ile Phe Ile Met
1               5                   10                  15

Ile Val Gly Gly Leu Ile Gly Leu Arg
            20                  25

<210> SEQ ID NO 34
<211> LENGTH: 25
<212> TYPE: PRT
<213> ORGANISM: Artificial Sequence
<220> FEATURE:
<223> OTHER INFORMATION: Peptide

<400> SEQUENCE: 34

Leu Ile Gly Leu Arg Ile Ile Leu Gly Val Leu Ser Ile Val Lys Arg
1               5                   10                  15

Val Arg Gln Gly Tyr Ser Pro Leu Ser
            20                  25
```

```
<210> SEQ ID NO 35
<211> LENGTH: 25
<212> TYPE: PRT
<213> ORGANISM: Artificial Sequence
<220> FEATURE:
<223> OTHER INFORMATION: Peptide

<400> SEQUENCE: 35

Tyr Ser Pro Leu Ser Phe Gln Thr Leu Pro Pro Asn Pro Arg Gly Pro
1               5                   10                  15

Asp Arg Leu Arg Gly Ile Glu Glu Glu
            20                  25

<210> SEQ ID NO 36
<211> LENGTH: 25
<212> TYPE: PRT
<213> ORGANISM: Artificial Sequence
<220> FEATURE:
<223> OTHER INFORMATION: Peptide

<400> SEQUENCE: 36

Gly Ile Glu Glu Glu Gly Gly Glu Gln Asp Lys Asp Arg Ser Ile Arg
1               5                   10                  15

Leu Val Ser Gly Phe Leu Ala Leu Val
            20                  25

<210> SEQ ID NO 37
<211> LENGTH: 25
<212> TYPE: PRT
<213> ORGANISM: Artificial Sequence
<220> FEATURE:
<223> OTHER INFORMATION: Peptide

<400> SEQUENCE: 37

Phe Leu Ala Leu Val Trp Glu Asp Leu Arg Ser Leu Cys Leu Phe Ser
1               5                   10                  15

Tyr His Arg Leu Arg Asp Phe Ile Leu
            20                  25

<210> SEQ ID NO 38
<211> LENGTH: 25
<212> TYPE: PRT
<213> ORGANISM: Artificial Sequence
<220> FEATURE:
<223> OTHER INFORMATION: Peptide

<400> SEQUENCE: 38

Arg Asp Phe Ile Leu Ile Ala Gly Arg Ala Ala Glu Leu Leu Gly Arg
1               5                   10                  15

Ser Ser Leu Arg Gly Leu Gln Thr Gly
            20                  25

<210> SEQ ID NO 39
<211> LENGTH: 25
<212> TYPE: PRT
<213> ORGANISM: Artificial Sequence
<220> FEATURE:
<223> OTHER INFORMATION: Peptide

<400> SEQUENCE: 39

Gly Leu Gln Thr Gly Trp Gln Ala Leu Lys Tyr Leu Gly Ser Leu Val
1               5                   10                  15

Gln Tyr Trp Gly Leu Glu Leu Lys Lys
            20                  25
```

```
<210> SEQ ID NO 40
<211> LENGTH: 25
<212> TYPE: PRT
<213> ORGANISM: Artificial Sequence
<220> FEATURE:
<223> OTHER INFORMATION: Peptide

<400> SEQUENCE: 40

Leu Glu Leu Lys Lys Ser Ala Ile Asn Leu Phe Asp Thr Thr Ala Ile
1               5                   10                  15

Val Val Ala Glu Gly Thr Asp Arg Leu
            20                  25

<210> SEQ ID NO 41
<211> LENGTH: 32
<212> TYPE: PRT
<213> ORGANISM: Artificial Sequence
<220> FEATURE:
<223> OTHER INFORMATION: Peptide

<400> SEQUENCE: 41

Gly Thr Asp Arg Leu Ile Glu Gly Leu Gln Gly Ile Gly Arg Ala Ile
1               5                   10                  15

Tyr Asn Ile Pro Arg Arg Ile Arg Gln Gly Phe Glu Ala Ala Leu Leu
            20                  25                  30

<210> SEQ ID NO 42
<211> LENGTH: 25
<212> TYPE: PRT
<213> ORGANISM: Artificial Sequence
<220> FEATURE:
<223> OTHER INFORMATION: Ref.F2.CMd

<400> SEQUENCE: 42

Lys Ile Asn Cys Thr Arg Pro Asn Asn Asn Thr Arg Lys Ser Ile Arg
1               5                   10                  15

Ile Gly Pro Gly Gln Val Phe Tyr Ala
            20                  25

<210> SEQ ID NO 43
<211> LENGTH: 25
<212> TYPE: PRT
<213> ORGANISM: Artificial Sequence
<220> FEATURE:
<223> OTHER INFORMATION: Ref.A2.CD

<400> SEQUENCE: 43

Pro Ile Asn Cys Thr Arg Pro Asn Asn Asn Thr Arg Lys Ser Ile Arg
1               5                   10                  15

Phe Gly Pro Gly Gln Ala Phe Tyr Thr
            20                  25

<210> SEQ ID NO 44
<211> LENGTH: 25
<212> TYPE: PRT
<213> ORGANISM: Artificial Sequence
<220> FEATURE:
<223> OTHER INFORMATION: Ref.C.BR

<400> SEQUENCE: 44

Glu Ile Asn Cys Thr Arg Pro Asn Asn Asn Thr Arg Lys Ser Ile Arg
1               5                   10                  15

Ile Gly Pro Gly Gln Ala Phe Tyr Ala
            20                  25
```

```
<210> SEQ ID NO 45
<211> LENGTH: 25
<212> TYPE: PRT
<213> ORGANISM: Artificial Sequence
<220> FEATURE:
<223> OTHER INFORMATION: Ref.F1.FI

<400> SEQUENCE: 45

Gln Ile Asn Cys Thr Arg Pro Asn Asn Asn Thr Arg Lys Ser Ile Arg
1               5                   10                  15

Ile Gly Pro Gly Gln Ser Phe Tyr Ala
            20                  25

<210> SEQ ID NO 46
<211> LENGTH: 25
<212> TYPE: PRT
<213> ORGANISM: Artificial Sequence
<220> FEATURE:
<223> OTHER INFORMATION: Ref.A1.KE

<400> SEQUENCE: 46

Thr Ile Lys Cys Ile Arg Pro Asn Asn Asn Thr Arg Lys Ser Ile Arg
1               5                   10                  15

Ile Gly Pro Gly Gln Ala Phe Tyr Ala
            20                  25

<210> SEQ ID NO 47
<211> LENGTH: 25
<212> TYPE: PRT
<213> ORGANISM: Artificial Sequence
<220> FEATURE:
<223> OTHER INFORMATION: Ref.A2.CY

<400> SEQUENCE: 47

Leu Ile Thr Cys Ile Arg Pro Asn Asn Asn Thr Arg Lys Ser Ile Arg
1               5                   10                  15

Phe Gly Pro Gly Gln Ala Phe Tyr Thr
            20                  25

<210> SEQ ID NO 48
<211> LENGTH: 25
<212> TYPE: PRT
<213> ORGANISM: Artificial Sequence
<220> FEATURE:
<223> OTHER INFORMATION: Ref.C.IN

<400> SEQUENCE: 48

Glu Ile Met Cys Thr Arg Pro Asp Asn Asn Thr Arg Lys Ser Ile Arg
1               5                   10                  15

Ile Gly Pro Gly Gln Thr Phe Tyr Ala
            20                  25

<210> SEQ ID NO 49
<211> LENGTH: 25
<212> TYPE: PRT
<213> ORGANISM: Artificial Sequence
<220> FEATURE:
<223> OTHER INFORMATION: Ref.D.TZ

<400> SEQUENCE: 49

Lys Ile Asn Cys Thr Arg Pro Asn Asn Asn Thr Arg Lys Gly Ile Arg
1               5                   10                  15

Ile Gly Pro Gly Gln Thr Phe Phe Thr
            20                  25
```

-continued

```
<210> SEQ ID NO 50
<211> LENGTH: 25
<212> TYPE: PRT
<213> ORGANISM: Artificial Sequence
<220> FEATURE:
<223> OTHER INFORMATION: Ref.A1.AU

<400> SEQUENCE: 50

Asn Ile Thr Cys Ile Arg Pro Asn Asn Asn Thr Arg Lys Ser Val Arg
1               5                   10                  15

Ile Gly Pro Gly Gln Thr Phe Tyr Ala
            20                  25

<210> SEQ ID NO 51
<211> LENGTH: 25
<212> TYPE: PRT
<213> ORGANISM: Artificial Sequence
<220> FEATURE:
<223> OTHER INFORMATION: Ref.A1.RW

<400> SEQUENCE: 51

Lys Ile Asn Cys Thr Arg Pro Asn Asn Asn Thr Arg Thr Ser Ile Arg
1               5                   10                  15

Ile Gly Pro Gly Gln Ser Phe His Ala
            20                  25

<210> SEQ ID NO 52
<211> LENGTH: 25
<212> TYPE: PRT
<213> ORGANISM: Artificial Sequence
<220> FEATURE:
<223> OTHER INFORMATION: Ref.A1.UG

<400> SEQUENCE: 52

Thr Ile Asn Cys Thr Arg Pro Asn Asn Asn Thr Arg Arg Ser Val Arg
1               5                   10                  15

Ile Gly Pro Gly Gln Thr Phe Tyr Ala
            20                  25

<210> SEQ ID NO 53
<211> LENGTH: 27
<212> TYPE: PRT
<213> ORGANISM: Artificial Sequence
<220> FEATURE:
<223> OTHER INFORMATION: Ref.B.FR

<400> SEQUENCE: 53

Glu Ile Asn Cys Thr Arg Pro Asn Asn Asn Thr Arg Lys Arg Ile Arg
1               5                   10                  15

Ile Gln Arg Gly Pro Gly Arg Ala Phe Val Thr
            20                  25

<210> SEQ ID NO 54
<211> LENGTH: 25
<212> TYPE: PRT
<213> ORGANISM: Artificial Sequence
<220> FEATURE:
<223> OTHER INFORMATION: Ref.B.NL

<400> SEQUENCE: 54

Glu Ile Asn Cys Thr Arg Pro Asn Asn Asn Thr Arg Lys Ser Ile His
1               5                   10                  15

Ile Gly Pro Gly Arg Ala Phe Tyr Ala
            20                  25
```

```
<210> SEQ ID NO 55
<211> LENGTH: 25
<212> TYPE: PRT
<213> ORGANISM: Artificial Sequence
<220> FEATURE:
<223> OTHER INFORMATION: Ref.C.ET

<400> SEQUENCE: 55

Glu Ile Thr Cys Thr Arg Pro Ser Asn Asn Thr Arg Glu Ser Ile Arg
1               5                   10                  15

Ile Gly Pro Gly Gln Thr Phe Tyr Ala
            20                  25

<210> SEQ ID NO 56
<211> LENGTH: 25
<212> TYPE: PRT
<213> ORGANISM: Artificial Sequence
<220> FEATURE:
<223> OTHER INFORMATION: Ref.F1.BR

<400> SEQUENCE: 56

Gln Ile Asn Cys Thr Arg Pro Asn Asn Asn Thr Arg Lys Arg Ile Ser
1               5                   10                  15

Leu Gly Pro Gly Arg Val Phe Tyr Thr
            20                  25

<210> SEQ ID NO 57
<211> LENGTH: 25
<212> TYPE: PRT
<213> ORGANISM: Artificial Sequence
<220> FEATURE:
<223> OTHER INFORMATION: Ref.F1.FR

<400> SEQUENCE: 57

Gln Ile Asn Cys Thr Arg Pro Asn Asn Asn Thr Arg Lys Ser Ile His
1               5                   10                  15

Leu Gly Pro Gly Gln Ala Phe Tyr Ala
            20                  25

<210> SEQ ID NO 58
<211> LENGTH: 25
<212> TYPE: PRT
<213> ORGANISM: Artificial Sequence
<220> FEATURE:
<223> OTHER INFORMATION: Ref.G.BE

<400> SEQUENCE: 58

Glu Ile Asn Cys Thr Arg Pro Asn Asn Asn Thr Arg Arg Ser Val Ala
1               5                   10                  15

Ile Gly Pro Gly Gln Ala Phe Tyr Thr
            20                  25

<210> SEQ ID NO 59
<211> LENGTH: 25
<212> TYPE: PRT
<213> ORGANISM: Artificial Sequence
<220> FEATURE:
<223> OTHER INFORMATION: Ref.G.NG

<400> SEQUENCE: 59

Glu Ile Asn Cys Ile Arg Pro Asn Asn Asn Thr Arg Lys Ser Ile Pro
1               5                   10                  15

Ile Gly Pro Gly Gln Ala Phe Tyr Ala
            20                  25
```

-continued

```
<210> SEQ ID NO 60
<211> LENGTH: 25
<212> TYPE: PRT
<213> ORGANISM: Artificial Sequence
<220> FEATURE:
<223> OTHER INFORMATION: Ref.H.BE

<400> SEQUENCE: 60

Gln Ile Asn Cys Thr Arg Thr Gly Asn Asn Thr Arg Lys Ser Ile Arg
1               5                   10                  15

Ile Gly Pro Gly Gln Ala Phe Tyr Ala
            20                  25

<210> SEQ ID NO 61
<211> LENGTH: 25
<212> TYPE: PRT
<213> ORGANISM: Artificial Sequence
<220> FEATURE:
<223> OTHER INFORMATION: Ref.J.SE

<400> SEQUENCE: 61

Glu Ile Val Cys Thr Arg Pro Asn Asn Asn Thr Arg Lys Gly Ile His
1               5                   10                  15

Met Gly Pro Gly Gln Val Leu Tyr Ala
            20                  25

<210> SEQ ID NO 62
<211> LENGTH: 25
<212> TYPE: PRT
<213> ORGANISM: Artificial Sequence
<220> FEATURE:
<223> OTHER INFORMATION: Ref.B.TH

<400> SEQUENCE: 62

Gln Ile Asn Cys Thr Arg Pro Asn Asn Asn Thr Arg Lys Ser Ile His
1               5                   10                  15

Met Gly Pro Gly Lys Ala Phe Tyr Thr
            20                  25

<210> SEQ ID NO 63
<211> LENGTH: 25
<212> TYPE: PRT
<213> ORGANISM: Artificial Sequence
<220> FEATURE:
<223> OTHER INFORMATION: Ref.B.TH

<400> SEQUENCE: 63

Glu Ile Asn Cys Thr Arg Pro Asn Asn Tyr Thr Arg Lys Arg Ile Thr
1               5                   10                  15

Met Gly Pro Gly Arg Val Tyr Tyr Thr
            20                  25

<210> SEQ ID NO 64
<211> LENGTH: 25
<212> TYPE: PRT
<213> ORGANISM: Artificial Sequence
<220> FEATURE:
<223> OTHER INFORMATION: Ref.F1.BE

<400> SEQUENCE: 64

Gln Ile Asn Cys Thr Arg Pro Asn Asn Asn Thr Arg Lys Gly Ile His
1               5                   10                  15

Leu Gly Pro Gly Gln Thr Phe Tyr Ala
            20                  25
```

```
<210> SEQ ID NO 65
<211> LENGTH: 25
<212> TYPE: PRT
<213> ORGANISM: Artificial Sequence
<220> FEATURE:
<223> OTHER INFORMATION: Ref.F2.CMa

<400> SEQUENCE: 65

Ile Ile Asp Cys Arg Arg Pro Asn Asn Thr Arg Lys Gly Ile Arg
1               5                   10                  15

Ile Gly Pro Gly Gln Thr Phe Phe Ala
            20                  25

<210> SEQ ID NO 66
<211> LENGTH: 25
<212> TYPE: PRT
<213> ORGANISM: Artificial Sequence
<220> FEATURE:
<223> OTHER INFORMATION: Ref.F2.CMb

<400> SEQUENCE: 66

Lys Ile Asn Cys Thr Arg Pro Asn Asn Thr Arg Arg Ser Ile His
1               5                   10                  15

Ile Gly Pro Gly Arg Ala Phe Tyr Ala
            20                  25

<210> SEQ ID NO 67
<211> LENGTH: 25
<212> TYPE: PRT
<213> ORGANISM: Artificial Sequence
<220> FEATURE:
<223> OTHER INFORMATION: Ref.F2.CMc

<400> SEQUENCE: 67

Ala Ile Asn Cys Thr Arg Pro Thr Asn Ile Thr Arg Arg Ser Met Arg
1               5                   10                  15

Ile Gly Pro Gly Arg Val Phe Tyr Ala
            20                  25

<210> SEQ ID NO 68
<211> LENGTH: 25
<212> TYPE: PRT
<213> ORGANISM: Artificial Sequence
<220> FEATURE:
<223> OTHER INFORMATION: Ref.G.PT

<400> SEQUENCE: 68

Pro Ile Thr Cys Ala Arg Pro Ser Asn Asn Thr Arg Lys Ser Ile Arg
1               5                   10                  15

Phe Gly Pro Gly Gln Ala Phe Tyr Ala
            20                  25

<210> SEQ ID NO 69
<211> LENGTH: 25
<212> TYPE: PRT
<213> ORGANISM: Artificial Sequence
<220> FEATURE:
<223> OTHER INFORMATION: Ref.H.BE

<400> SEQUENCE: 69

Glu Ile Thr Cys Thr Arg Pro Asn Asn Thr Arg Lys Gly Ile His
1               5                   10                  15

Phe Gly Pro Gly Gln Ala Phe Tyr Ala
            20                  25
```

```
<210> SEQ ID NO 70
<211> LENGTH: 25
<212> TYPE: PRT
<213> ORGANISM: Artificial Sequence
<220> FEATURE:
<223> OTHER INFORMATION: Ref.J.SE

<400> SEQUENCE: 70

Glu Ile Val Cys Tyr Arg Pro Asn Asn Thr Arg Lys Gly Ile His
1               5                   10                  15

Met Gly Pro Gly Gln Val Leu Tyr Ala
            20                  25

<210> SEQ ID NO 71
<211> LENGTH: 25
<212> TYPE: PRT
<213> ORGANISM: Artificial Sequence
<220> FEATURE:
<223> OTHER INFORMATION: Ref.K.CD

<400> SEQUENCE: 71

Glu Ile Asn Cys Thr Arg Pro Ser Asn Asn Thr Arg Lys Ser Ile His
1               5                   10                  15

Ile Gly Pro Gly Arg Ala Phe Tyr Ala
            20                  25
```